US010667774B2

(12) United States Patent
Kato et al.

(10) Patent No.: US 10,667,774 B2
(45) Date of Patent: Jun. 2, 2020

(54) X-RAY CT APPARATUS

(71) Applicant: Canon Medical Systems Corporation, Otawara-shi (JP)

(72) Inventors: Tooru Kato, Nasushiobara (JP); Hiroaki Miyazaki, Otawara (JP); Emi Tamura, Yokohama (JP); Hiroaki Nakai, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 13 days.

(21) Appl. No.: 16/041,224

(22) Filed: Jul. 20, 2018

(65) Prior Publication Data

US 2019/0021687 A1 Jan. 24, 2019

(30) Foreign Application Priority Data

Jul. 20, 2017 (JP) .................. 2017-141320
Jul. 20, 2018 (JP) .................. 2018-136375

(51) Int. Cl.
*A61B 6/00* (2006.01)
*A61B 6/03* (2006.01)
*A61B 6/06* (2006.01)

(52) U.S. Cl.
CPC ............ *A61B 6/4488* (2013.01); *A61B 6/032* (2013.01); *A61B 6/035* (2013.01); *A61B 6/06* (2013.01); *A61B 6/4035* (2013.01); *A61B 6/4233* (2013.01); *A61B 6/4241* (2013.01); *A61B 6/5205* (2013.01); *A61B 6/54* (2013.01)

(58) Field of Classification Search
CPC .............................. A61B 6/032; A61B 6/4241
See application file for complete search history.

(56) References Cited

U.S. PATENT DOCUMENTS

| 9,229,115 | B2 | 1/2016 | Griesmer et al. |
| 2003/0016779 | A1 | 1/2003 | Pohan et al. |
| 2011/0291017 | A1 | 12/2011 | Frach |
| 2013/0248729 | A1 | 9/2013 | Hannemann et al. |
| 2015/0076357 | A1 | 3/2015 | Frach |
| 2016/0084964 | A1 | 3/2016 | Kimura et al. |
| 2018/0292551 | A1* | 10/2018 | Danielsson ............. G01T 7/005 |

FOREIGN PATENT DOCUMENTS

| JP | 4-315985 | 11/1992 |
| JP | 10-234722 | 9/1998 |
| JP | 2003-130961 | 5/2003 |

* cited by examiner

*Primary Examiner* — Dani Fox
(74) *Attorney, Agent, or Firm* — Oblon, McClelland, Maier & Neustadt, L.L.P.

(57) ABSTRACT

An X-ray CT apparatus according to an embodiment includes a photon counting detector and processing circuitry. The photon counting detector includes a plurality of detection areas arranged in a channel direction and a column direction and is configured to output detection signals corresponding to the quantity of photons incident thereto, the detection areas each including a plurality of detecting elements. The processing circuitry is configured to calculate a heat generation amount for each of the detection areas on the basis of the detection signal corresponding to the incident photons detected in the detection area, to determine a control amount on the basis of the heat generation amount calculated for each of the detection areas, and to control temperature in each of the detection areas by using the determined control amount.

20 Claims, 16 Drawing Sheets

FIG.2
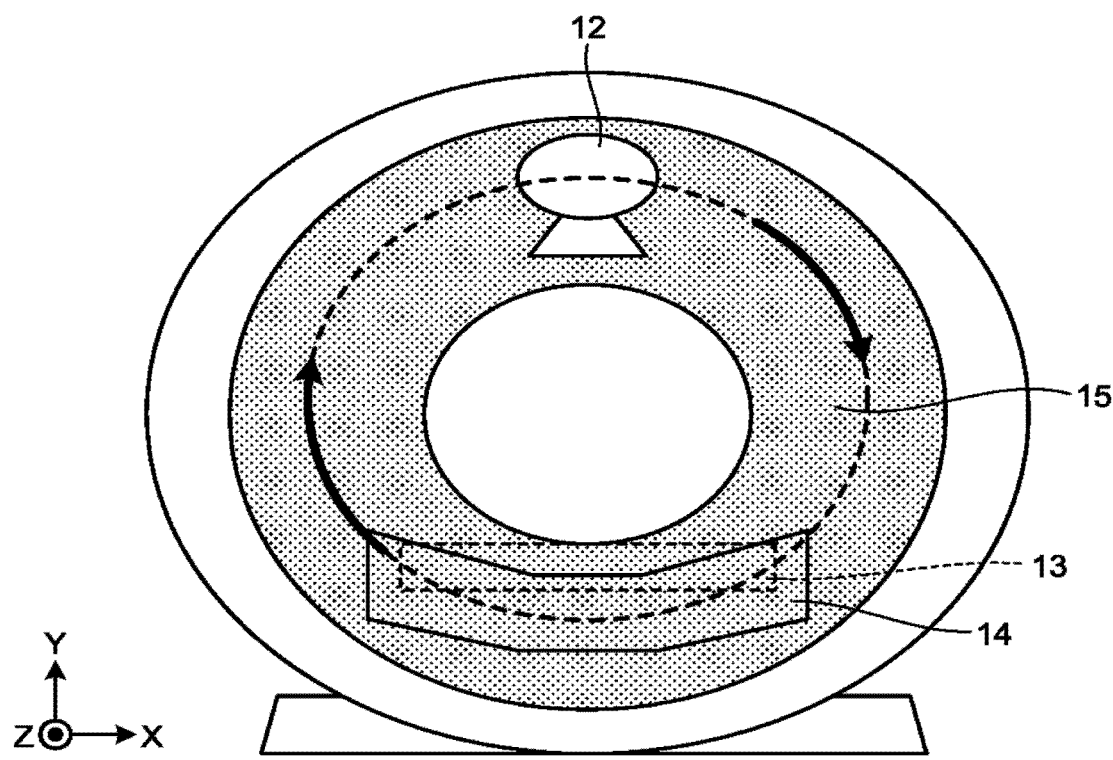
FIG.3
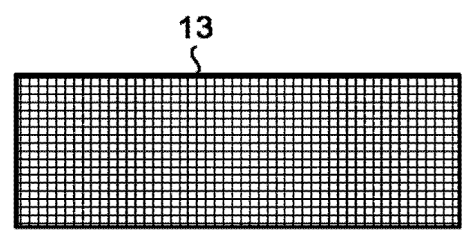
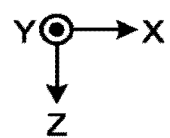

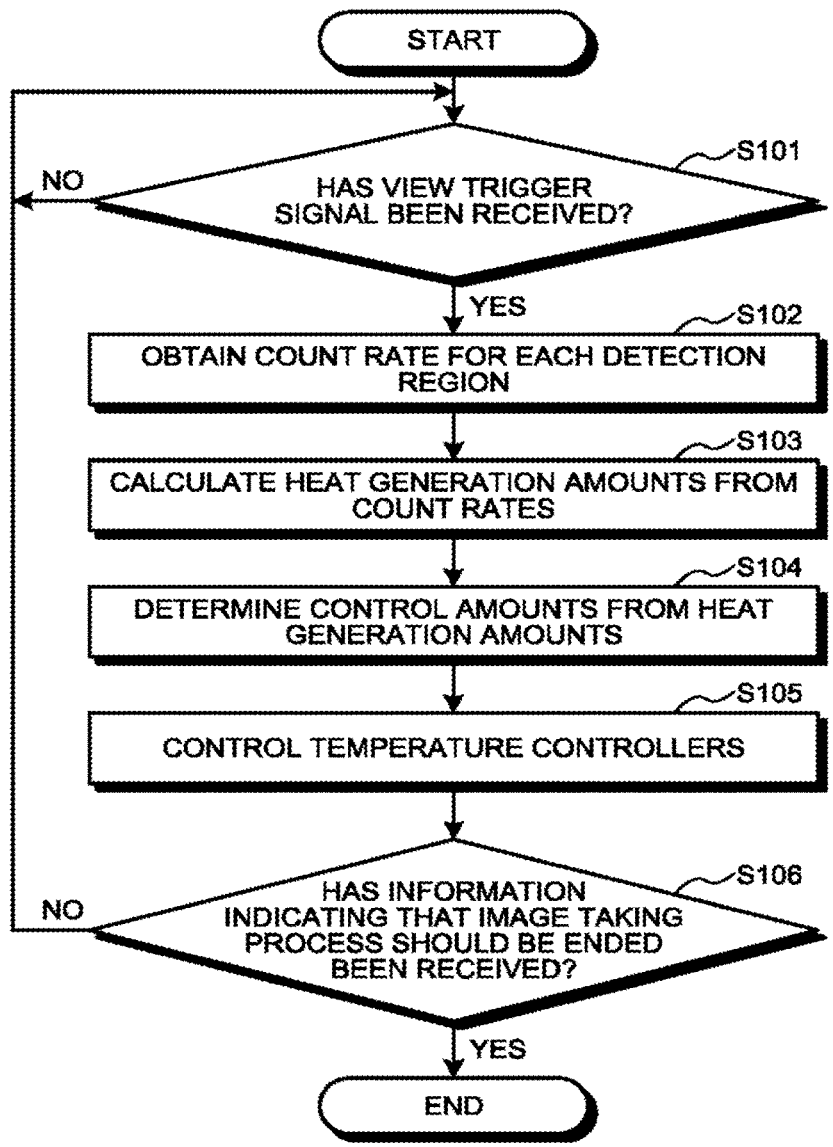

| DETECTION AREA ID | HEAT GENERATION AMOUNT | CONTROL AMOUNT |
|---|---|---|
| A1 | Q1 | R1 |
| | Q2 | R2 |
| | Q3 | R3 |
| | Q4 | R4 |
| A2 | Q1 | R2 |
| ... | ... | ... |

FIG.14

| DETECTION AREA ID | HEAT GENERATION AMOUNT | EXTERNAL TEMPERATURE | CONTROL AMOUNT |
|---|---|---|---|
| A1 | Q1 | T<T1 | R11 |
| | | T1≤T<T2 | R12 |
| | | T2≤T | R13 |
| | Q2 | T<T1 | R21 |
| | | T1≤T<T2 | R22 |
| | | T2≤T | R23 |
| ... | ... | ... | ... |

FIG.18

| CHANGE AMOUNT IN COUNT RATE | CONTROL AMOUNT | CORRECTION AMOUNT |
|---|---|---|
| $\Delta C < C11$ | R111 | $\alpha 1$ |
|  | R112 | $\alpha 2$ |
|  | R113 | $\alpha 3$ |
| $C11 \leq \Delta C < C12$ | ... | ... |
|  | ... | ... |
|  | ... | ... |
| $C12 \leq \Delta C < C13$ | ... | ... |
| $C13 \leq \Delta C$ | ... | ... |

| COUNT RATE IN SCANOGRAM TAKING PROCESS | COUNT RATE IN MAIN IMAGE TAKING PROCESS |
|---|---|
| $C < C5$ | $C < C1$ |
| $C5 \leq C < C6$ | $C1 \leq C < C2$ |
| $C6 \leq C < C7$ | $C2 \leq C < C3$ |
| $C7 \leq C$ | $C3 \leq C$ |

# X-RAY CT APPARATUS

CROSS-REFERENCE TO RELATED APPLICATIONS

This application is based upon and claims the benefit of priority from Japanese Patent Application No. 2017-141320, filed on Jul. 20, 2017; and Japanese Patent Application No. 2018-136375, filed on Jul. 20, 2018; the entire contents of which are incorporated herein by reference.

FIELD

Embodiments described herein relate generally to an X-ray Computed Tomography (CT) apparatus.

BACKGROUND

When a detector of a photon counting type (hereinafter, "photon counting detector") is structured as an area detector, Application Specific Integrated Circuits (ASICs) are arranged in a highly concentrated manner to be positioned very close to the photon counting detector, to measure small output electric currents from the photon counting detector. While acquiring count results, the ASICs generate heat in accordance with count rates thereof. Because the ASICs are arranged in the vicinity of the photon counting detector, the heat generated by the ASICs is easily transferred to the detector.

To cope with this situation, a method has been proposed by which a heater is provided in the vicinity of a photon counting detector so as to exercise control to keep the photon counting detector at a constant temperature by using an output from a temperature sensor as a control signal. Further, another method has also been proposed by which, without using a temperature sensor, the temperature of a photon counting detector is controlled by conjecturing the temperature on the basis of a dark current value obtained from the photon counting detector prior to a scan.

BRIEF DESCRIPTION OF THE DRAWINGS

FIG. 2 is a front view of a gantry according to the first embodiment;

FIG. 3 is a drawing for explaining an example of a detector according to the first embodiment;

FIG. 8 is a flowchart illustrating a procedure performed by the X-ray CT apparatus according to the first embodiment to perform a temperature controlling process;

FIG. 9 is a table illustrating an example of information stored in first correspondence information according to the first embodiment;

FIG. 14 is a table illustrating an example of information stored in second correspondence information according to the second embodiment;

FIG. 18 is a table illustrating an example of information stored in third correspondence information according to the third embodiment;

DETAILED DESCRIPTION

An X-ray Computed Tomography (CT) apparatus according to an embodiment includes a photon counting detector and processing circuitry. The photon counting detector includes a plurality of detection areas arranged in a channel direction and a column direction and is configured to output detection signals corresponding to the quantity of photons incident thereto, the detection areas each including a plurality of detecting elements. The processing circuitry is configured to calculate a heat generation amount for each of the detection areas on the basis of the detection signal corresponding to the incident photons detected in the detection area, to determine a control amount on the basis of the heat generation amount calculated for each of the detection areas, and to control temperature in each of the detection areas by using the determined control amount.

Exemplary embodiments of an X-ray CT apparatus will be explained below, with reference to the drawings.

The X-ray CT apparatuses described in the embodiments below are each an apparatus capable of executing a photon counting CT procedure. In other words, the X-ray CT apparatuses described in the embodiments below are each an apparatus capable of reconstructing X-ray CT image data having a high Signal-to-Noise (S/N) ratio, by counting X-rays that have passed through an examined subject, while employing not a conventional integral detector (that implements a current mode measuring method), but a detector that implements a photon counting method. The description in each of the embodiments is, in principle, applicable to any other embodiment.

First Embodiment

Figure 1:
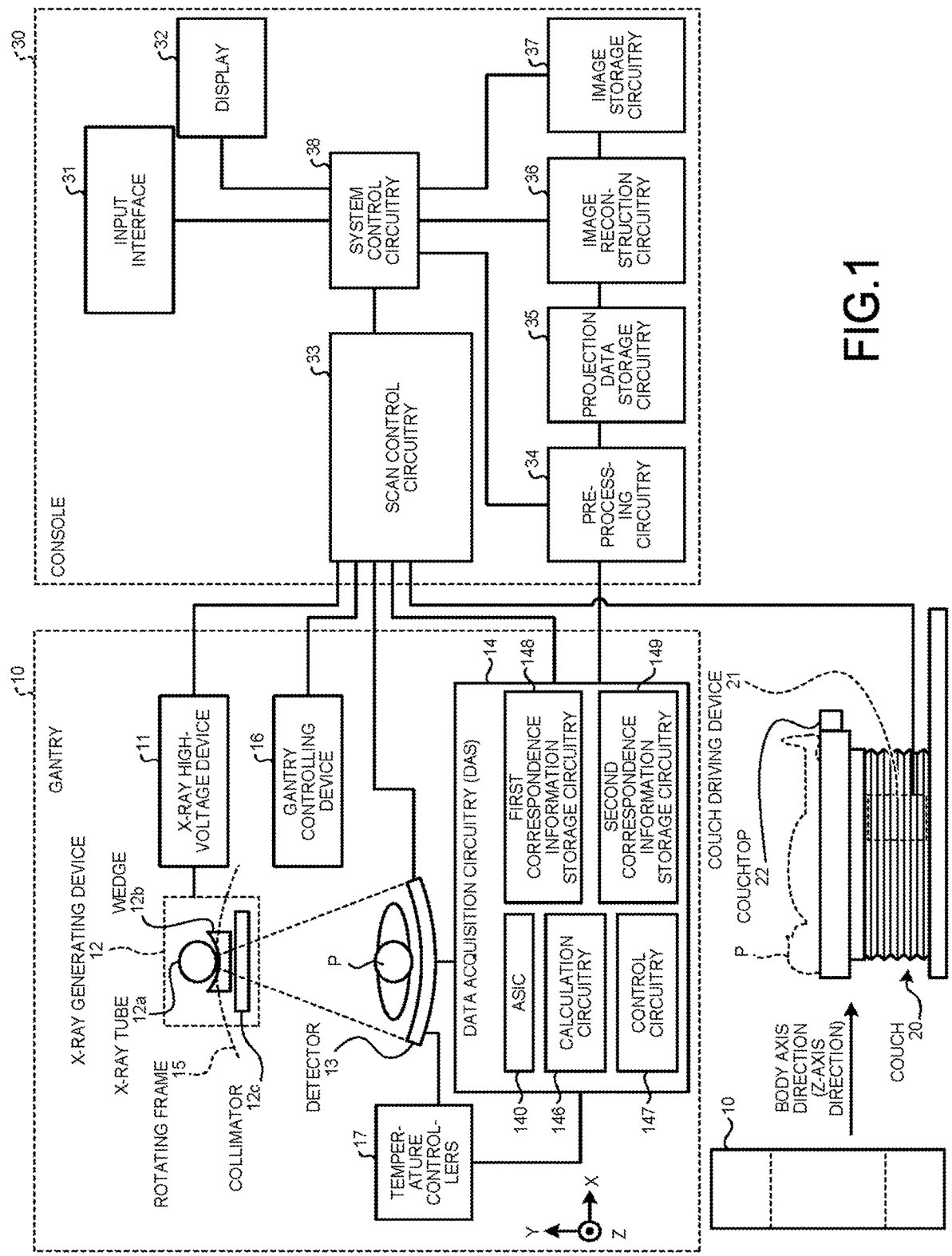
FIG. 1 is a block diagram illustrating an exemplary configuration of an X-ray CT apparatus according to a first embodiment.

FIG. 1 is a block diagram illustrating an exemplary configuration of an X-ray CT apparatus according to a first embodiment. As illustrated in FIG. 1, the X-ray CT apparatus according to the first embodiment includes a gantry 10, a couch 20, and a console 30.

The gantry 10 is a device configured to radiate X-rays onto an examined subject (hereinafter, "patient") P and to acquire data related to X-rays that have passed through the patient P. The gantry 10 includes an X-ray high-voltage device 11, an X-ray generating device 12, a detector 13, data acquisition circuitry 14, a rotating frame 15, a gantry controlling device 16, and a temperature controller 17. Further, as illustrated in FIG. 1, by the gantry 10, an orthogonal coordinate system structured with an X-axis, a Y-axis, and a Z-axis is defined. In other words, the X-axis expresses the horizontal direction, while the Y-axis expresses the vertical direction, and the Z-axis expresses the axial direction of the rotation center of the rotating frame 15 observed while the gantry 10 is not tilted.

FIG. 2 is a front view of the gantry 10 according to the first embodiment. As illustrated in FIG. 2, the rotating frame 15 is an annular frame configured to support the X-ray generating device 12 and the detector 13 so as to oppose each other while the patient P is interposed therebetween and configured to be rotated by the gantry controlling device 16 (explained later) at a high speed on a circular orbit centered on the patient P.

The X-ray generating device 12 is a device configured to generate the X-rays and to radiate the generated X-rays onto the patient P. The X-ray generating device 12 includes an X-ray tube 12a, a wedge 12b, and a collimator 12c.

Returning to the description of FIG. 1, the X-ray tube 12a is a vacuum tube configured to emit thermo electrons from a negative pole (which may be referred to as a filament) to a positive pole (a target), by receiving a supply of high voltage from the X-ray high-voltage device 11. The X-ray tube 12a radiates an X-ray beam onto the patient P, as the rotating frame 15 rotates. In other words, the X-ray tube 12a is configured to generate the X-rays by using the high voltage supplied thereto from the X-ray high-voltage device 11.

Further, the X-ray tube 12a is configured to generate the X-ray beam that spreads with a fan angle and a cone angle. For example, under control of the X-ray high-voltage device 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray high-voltage device 11, the X-ray tube 12a is capable of intermittently emitting X-rays (pulse X-rays) in positions (X-ray tube positions) set in advance. Further, the X-ray high-voltage device 11 is also capable of modulating intensities of the X-rays emitted from the X-ray tube 12a. For example, the X-ray high-voltage device 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is configured by using a lead plate or the like and has a slit in a part thereof. For example, by using the slit, the collimator 12c is configured to narrow down the radiation range of the X-rays of which the X-ray dose has been adjusted by the wedge 12b, under the control of the X-ray high-voltage device 11 (explained later).

Possible X-ray sources of the X-ray generating device 12 are not limited to the X-ray tube 12a. For example, in place of the X-ray tube 12a, the X-ray generating device 12 may be structured with a focus coil configured to converge an electron beam generated by an electron gun, a deflection coil configured to electromagnetically deflects the electron beam, and a target ring that covers a half of the surrounding of the patient P and is configured to generate X-rays by having the deflected electron beam collide thereon.

The X-ray high-voltage device 11 is configured by using an electric circuit such as a transformer, a rectifier, and the like and is structured with a high-voltage generating device having a function of generating the high voltage to be applied to the X-ray tube 12a and an X-ray controlling device configured to control the output voltage in accordance with the X-rays to be radiated by the X-ray tube 12a. The high-voltage generating device may be of a transformer type or of an inverter type. For example, by adjusting the X-ray tube voltage and the X-ray tube current supplied to the X-ray tube 12a, the X-ray high-voltage device 11 adjusts the dose of the X-rays radiated onto the patient P. Further, the X-ray high-voltage device 11 is subject to control of scan control circuitry 33 included in the console 30.

The gantry controlling device 16 is structured with: processing circuitry configured by using a Central Processing Unit (CPU) or the like; and a driving mechanism configured by using a motor, an actuator, and the like. The gantry controlling device 16 has a function of controlling operations of the gantry 10 by receiving an input signal from either an input interface 31 attached to the console 30 or an input interface attached to the gantry 10. For example, the gantry controlling device 16 exercises control to cause the X-ray tube 12a and the detector 13 to revolve on a circular orbit centered on the patient P, by rotating the rotating frame 15 upon receipt of the input signal, exercises control to tilt the gantry 10, and exercises control to operate the couch 20 and a couchtop 22. The gantry controlling device 16 is subject to control of the scan control circuitry 33 included in the console 30.

Further, the gantry controlling device 16 is configured to monitor the position of the X-ray tube 12a. When the X-ray tube 12a has reached a predetermined rotation angle (an image taking angle), the gantry controlling device 16 outputs, to the data acquisition circuitry 14, a view trigger signal indicating timing with which a data taking-in process should be started. For example, when the total number of views during a rotating imaging process is 2,400, the gantry controlling device 16 outputs a view trigger signal every time the X-ray tube 12a moves on the circular orbit by 0.15 degrees (=360/2,400).

Returning to the description of FIG. 1, the temperature controller 17 is configured to control the temperature of the detector 13. For example, the temperature controller 17 controls the temperature of the detector 13, on the basis of a control amount determined by control circuitry 147 (explained later). In the present example, the temperature controller 17 is a thermoelectric conversion device configured with, for example, a Peltier element or the like. In that situation, as the control amount, the temperature controller 17 receives, for example, the polarity of an electric current and the level of the electric current from the control circuitry 147.

The temperature controller 17 does not necessarily have to be configured by using a thermoelectric conversion device such as a Peltier element. As long as the temperature controller 17 is able to control the temperature of the detector 13, the temperature controller 17 may be of an air cooling type or of a water cooling type, for example. When being of an air cooling type, the temperature controller 17 may be a fan, for example, and may be configured to receive a rotating speed of the fan as the control amount from the control circuitry 147. As another example, when being of a water cooling type, the temperature controller 17 may be structured by using cooling water and a radiator, for example, and may be configured to receive a cooling air amount used for cooling the radiator as the control amount from the control circuitry 147.

The detector 13 is a photon counting detector that includes a plurality of X-ray detecting elements (which may be referred to as "sensors" or simply "detecting elements") configured to count light occurring from the X-rays that have passed through the patient P. In one example, the X-ray detecting elements included in the detector 13 according to the first embodiment are each an area detector of an indirect conversion type structured with a scintillator and an optical sensor. In the present example, for instance, the optical sensor is a Silicon PhotoMultiplier (SiPM). Alternatively, the detector 13 may be a detector of a direct conversion type structured with a semiconductor element configured to convert an X-ray incident thereto, into an electrical signal. The detector 13 is an example of the photon counting detector.

Each of the X-ray detecting elements included in the detector 13 is configured to output an electrical signal (a pulse) corresponding to the X-ray photons that have become incident thereto. The electrical signals output by the X-ray detecting elements may be referred to as detection signals. In other words, the detector 13 includes the plurality of detecting elements and is configured to output the detection signals corresponding to the quantity of photons incident thereto. The peak value of each of the electrical signals (the pulses) has correlation with energy values of the X-ray photons. FIG. 3 is a drawing for explaining an example of the detector 13 according to the first embodiment.

FIG. 3 is an enlarged view of the detector 13 illustrated in FIG. 2. FIG. 3 illustrates the detector 13 as being viewed from the Y-axis side. As illustrated in FIG. 3, in the detector 13, the X-ray detecting elements are two-dimensionally arranged on a plane. For example, a plurality of rows of X-ray detecting elements are arranged along the body axis (the column) direction of the patient P (the Z-axis direction in FIG. 3), the rows each being made up of a plurality of X-ray detecting elements arranged along the channel direction (the X-axis direction in FIG. 3). In other words, the detector 13 includes the plurality of detecting elements arranged in the channel direction and the column direction.

Figure 4A:
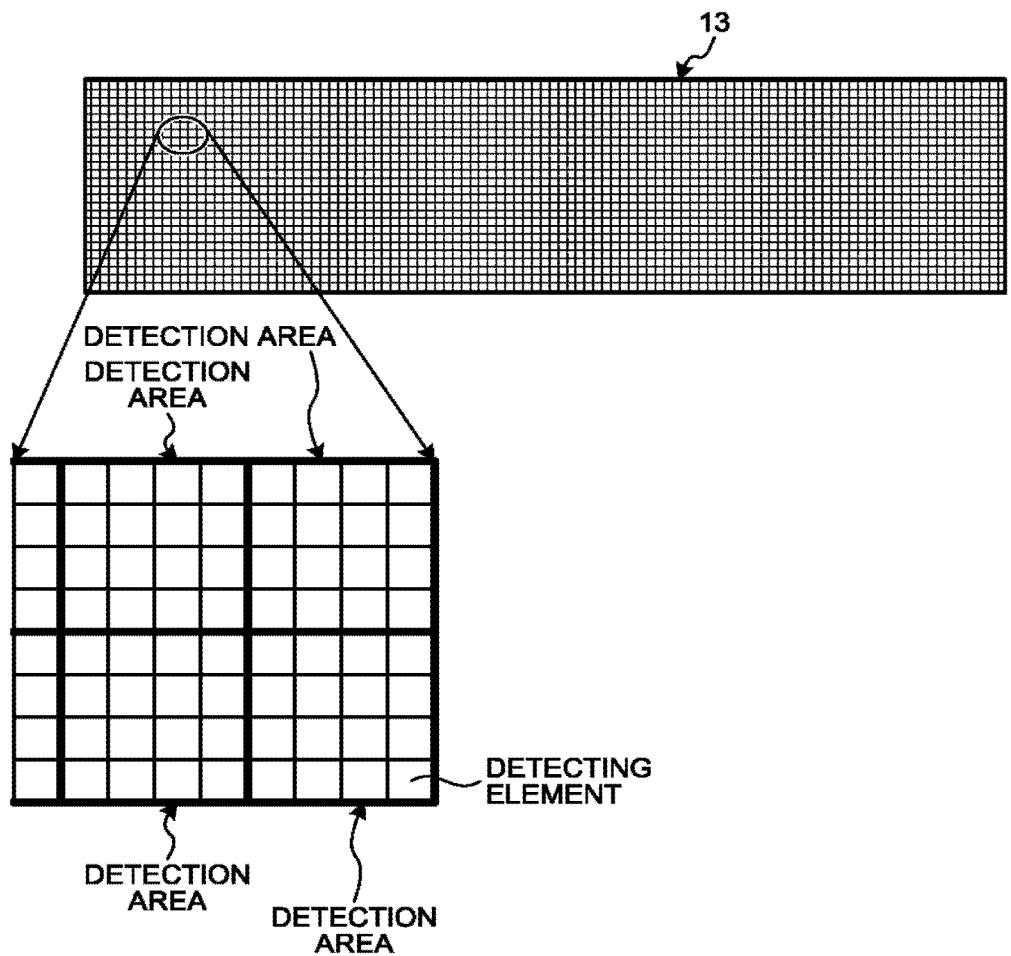
FIG. 4A is a drawing for explaining a structure of the detector according to the first embodiment.
Figure 4B:
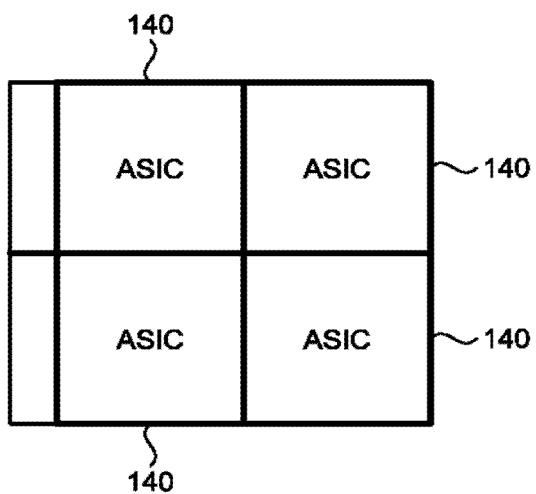
FIG. 4B is another drawing for explaining the structure of the detector according to the first embodiment.

Further, the detector 13 configured as the multi-column area detector has a plurality of detection areas each including two or more of the detecting elements. FIGS. 4A and 4B are drawings for explaining a structure of the detector 13 according to the first embodiment. FIG. 4A illustrates the detector 13 as being viewed from the incident surface side. Further, FIG. 4A includes an enlarged view of a region positioned in an upper left section of the detector 13.

As illustrated in FIG. 4A, the detector 13 has the plurality of detection areas. The example in FIG. 4A illustrates four detection areas of which one unit is made up of four columns and four channels. In other words, in FIG. 4A, each of the detection areas contains sixteen detecting elements. Further, in the detector 13 according to the first embodiment, the temperature controller 17 is provided for each of the detection areas. In other words, each of the temperature controllers 17 is configured to control the temperature of a corresponding one of the plurality of detection areas of the detector 13, which is configured as a photon counting detector.

The example in FIG. 4B illustrates the region of the enlarged view in FIG. 4A as being viewed from the rear side of the incident surface. On the rear side of the incident surface of the detector 13, an ASIC 140 (explained later) is arranged in each of the detection areas. Although FIG. 4A illustrates the example in which each single unit of the detection areas is made up of four columns and four channels, the number of detecting elements contained in each of the detection areas is not limited to that in the present example and may arbitrarily be modified. For instance, the detection areas may be modules of which one unit is made up of sixteen columns and six channels.

Returning to the description of FIG. 1, the data acquisition circuitry 14 is electric processing circuitry having a function of acquiring a count result, which is a result of the counting process using the detection signals of the detector 13. The data acquisition circuitry 14 is configured to count the photons (the X-ray photons) occurring from the X-rays that were emitted from the X-ray tube 12a and have passed through the patient P and to acquire a result of discriminating energy levels of the counted photons as the count result. After that, the data acquisition circuitry 14 transmits the count result to the console 30. The data acquisition circuitry 14 may be referred to as a Data Acquisition System (DAS).

Figure 5:
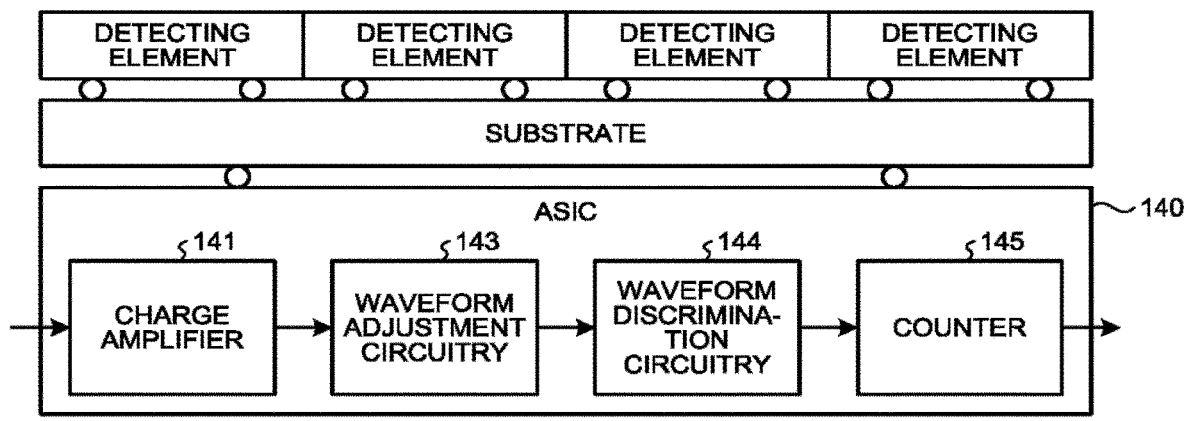
FIG. 5 is a block diagram illustrating an exemplary configuration of ASICs according to the first embodiment.

Further, for example, as illustrated in FIG. 1, the data acquisition circuitry 14 includes the Application Specific Integrated Circuits (ASICs) 140, calculation circuitry 146, the control circuitry 147, first correspondence information storage circuitry 148, and second correspondence information storage circuitry 149. In this situation, when the detector 13 is structured as an area detector, it is necessary to arrange the ASICs 140 in a highly concentrated manner to be positioned very close to the detector 13, to measure small output electric currents from the detector 13. FIG. 5 is a block diagram illustrating an exemplary configuration of the ASICs 140 according to the first embodiment.

As illustrated in FIG. 5, each of the ASICs 140 is connected to the detecting elements of the detector 13 via a substrate. In this situation, via the substrate, for example, each of the ASICs 140 is connected to two or more detecting elements contained in mutually the same detection area. Further, each of the ASICs 140 is configured to receive detection signals from the two or more detecting elements. Further, each of the ASICs 140 is configured to acquire a count result of the corresponding area. In other words, on the basis of the detection signals corresponding to the incident photons detected in the corresponding detection area, each of the ASICs 140 is configured to calculate a count rate. In that situation, each of the ASICs 140 may receive the detection signals from the two or more detecting elements parallel to one another or may receive the detection signals from the two or more detecting elements in a time-division manner. Although FIG. 5 illustrates only one ASIC 140, it is also acceptable to install two or more ASICs 140 in each of the detection areas. When two or more ASICs 140 are installed in each of the detection areas, each of the ASICs 140 in each area may receive one or more detection signal from one or more detecting elements in a corresponding region within the area or may receive detection signals from all the detecting elements in the areas. When each of the ASICs 140 receives one or more detection signals from one or more detecting elements in a corresponding region within the area, a total of the detection signals received by the ASICs 140 may be used as a count result. When each of the ASICs 140 receives detection signals from all the detecting elements in the area, an average of the detection signals received by the ASICs 140 may be used as a count result.

Further, as illustrated in FIG. 5, each of the ASICs 140 includes a charge amplifier 141, waveform adjustment circuitry 143, waveform discrimination circuitry 144, and a counter 145. The charge amplifier 141 is an electric circuit having a function of integrating and amplifying electric charges collected in response to the photons incident to the X-ray detecting elements and further outputting the result as a pulse signal indicating the quantity of electricity. More specifically, the charge amplifier 141 is an electronic circuit having the amplifying function. The pulse signal output by the charge amplifier 141 has a wave peak and an area corresponding to the energy amount of the photons. To an output side of the charge amplifier 141, the waveform adjustment circuitry 143 is connected.

The waveform adjustment circuitry 143 is configured to adjust the waveform of the pulse signal by adjusting frequency characteristics of the pulse signal output from the charge amplifier 141 and further applying a gain and an offset thereto. To an output side of the waveform adjustment circuitry 143, the waveform discrimination circuitry 144 is connected.

The waveform discrimination circuitry 144 is electric processing circuitry having a function of comparing either the wave peak or the area of a response pulse signal responsive to the incident photons with a threshold value that is set in advance in correspondence with a plurality of energy bands subject to a discrimination process and further outputting a result of the comparison with the threshold value to the counter 145 provided at the subsequent stage.

The counter 145 is an electric circuit having a function of counting a result of the discrimination process performed on the waveform of the response pulse signal for each of the corresponding energy bands and further outputting the photon count result as digital data to pre-processing circuitry 34 included in the console 30. More specifically, the counter 145 is a digital circuit configured to process numerical values by counting clock pulses, for example.

More specifically, the counter 145 is configured to acquire, as the count result, incident positions (detection positions) of X-ray photons that were counted by discriminating the pulses output by the X-ray detecting elements and energy values of the X-ray photons, for each of the phases of the X-ray tube 12*a* (X-ray tube phases). For example, the counter 145 uses the position of each of the X-ray detecting elements that output the pulses used for the counting process, as the incident position.

For example, the count result acquired by the counter 145 is information indicating that "with respect to an X-ray tube phase "α1", for an X-ray detecting element positioned at the incident position "P11", the count value of the photons in the energy discrimination band "E1<E≤E2" is "N1", whereas the count value of the photons in the energy discrimination band "E2<E≤E3" is "N2"". In another example, the count result acquired by the counter 145 is information indicating that "with respect to the X-ray tube phase "α1", for the X-ray detecting element positioned at the incident position "P11", the count value per unit time period of the photons in the energy discrimination band "E1<E≤E2" is "n1", whereas the count value per unit time period of the photons in the energy discrimination band "E2<E≤E3" is "n2"".

In this manner, from the X-ray detecting element in the detector 13 corresponding to any single pixel, a count result corresponding to the plurality of energy bands is output as detection data to the pre-processing circuitry 34. As a result, image reconstruction circuitry 36 is configured to generate an image by using the proofed detection signals from the detecting elements.

In the present example, the data output from the data acquisition circuitry 14 may be referred to as detection data. In contrast, data obtained by applying one or more pre-processing processes such as a logarithmic conversion process, an offset correcting process, an inter-channel sensitivity correcting process, an inter-channel gain correcting process, a pile-up correcting process, a response function correcting process, a beam hardening correcting process, and/or the like, to the detection data may be referred to as raw data. Further, the detection data and the raw data may collectively be referred to as projection data. The calculation circuitry 146, the control circuitry 147, the first correspondence information storage circuitry 148, and the second correspondence information storage circuitry 149 will be explained later.

Returning to the description of FIG. 1, the couch 20 is a device on which the patient P is placed and includes the couchtop 22 and a couch driving device 21. The couchtop 22 is a plate on which the patient P is placed. The couch driving device 21 is configured to move the patient P to the inside of the rotating frame 15 by moving the couchtop 22 in the Z-axis direction. The couch driving device 21 is also capable of moving the couchtop 22 in the X-axis directions.

As for methods of moving the couchtop 22, it is acceptable to move only the couchtop 22. Alternatively, it is also acceptable to move the couch 20 from the base thereof. Further, when a standing CT process is performed, another method is also acceptable in which a patient moving mechanism corresponding to the couchtop 22 is moved.

Further, for example, the gantry 10 performs a helical scan by which the patient P is helically scanned by causing the rotating frame 15 to rotate while the couchtop 22 is being moved. In another example, the gantry 10 performs a conventional scan by which the patient P is scanned on a circular orbit by causing the rotating frame 15 to rotate, while the position of the patient P is being fixed after the couchtop 22 is moved. In the embodiments described below, examples will be explained in which the relative position between the gantry 10 and the couchtop 22 can be changed by controlling the couchtop 22; however, possible embodiments are not limited to this example. For instance, when the gantry 10 is self-propelled, the relative position between the gantry 10 and the couchtop 22 may be changed by controlling the self-propelled movement of the gantry 10. Alternatively, the relative position between the gantry 10 and the couchtop 22 may be changed by controlling the movement of the gantry 10 and the couchtop 22.

The console 30 is a device configured to receive operations performed by the operator on the X-ray CT apparatus and also configured to reconstruct X-ray CT image data by using the count results acquired by the gantry 10. As illustrated in FIG. 1, the console 30 includes the input interface 31, a display 32, the scan control circuitry 33, the pre-processing circuitry 34, projection data storage circuitry 35, the image reconstruction circuitry 36, image storage circuitry 37, and system control circuitry 38.

The input interface 31 includes a mouse, a keyboard, and/or the like used by the operator of the X-ray CT apparatus for inputting various types of instructions and various types of settings and is configured to transfer information about the instructions and the settings received from the operator to the system control circuitry 38. For example, the input interface 31 is configured to receive, from the operator, a reconstruction condition used when X-ray CT image data is reconstructed, an image processing condition used for the X-ray CT image data, and/or the like. Further, for example, the input interface 31 is configured to receive an instruction from the operator indicating that a temperature controlling process should be performed on the X-ray detecting elements. Further, the input interface 31 is configured to instruct the scan control circuitry 33 to perform the X-ray CT image data reconstruction process and the temperature controlling process, via the system control circuitry 38.

The display 32 is a monitor referenced by the operator and is configured, under control of the system control circuitry 38, to display the X-ray CT image data for the operator and to display a Graphical User Interface (GUI) used for receiving the various types of instructions and the various types of settings from the operator via the input interface 31.

The scan control circuitry 33 is electric processing circuitry having a function of controlling the count result acquiring process performed by the gantry 10, by controlling operations of the X-ray high-voltage device 11, the detector 13, the gantry controlling device 16, the data acquisition circuitry 14, and the couch driving device 21 under the control of the system control circuitry 38 (explained later).

The pre-processing circuitry 34 is electric processing circuitry having a function of generating the raw data by performing, on the count result transmitted thereto from the data acquisition circuitry 14, one or more pre-processing processes such as a logarithmic conversion process, an offset correcting process, an inter-channel sensitivity correcting process, an inter-channel gain correcting process, a pile-up correcting process, a response function correcting process, a beam hardening correcting process, and/or the like.

The projection data storage circuitry 35 is configured by using, for example, a Not And (NAND) flash memory, a Hard Disk Drive (HDD), or the like and is configured to store therein the projection data generated by the pre-processing circuitry 34. In other words, the projection data storage circuitry 35 is configured to store therein the projection data used for reconstructing the X-ray CT image data.

The image reconstruction circuitry 36 is configured to generate the X-ray CT image data by performing a reconstruction process that uses a filter correction back projection method, a successive approximation reconstruction method, or the like, on the projection data generated by the pre-processing circuitry 34.

The image reconstruction circuitry 36 is configured to store the reconstructed X-ray CT image data into the image storage circuitry 37. In this situation, X-ray CT image data reconstructed from data including total energy information by adding together pieces of information of all the bins in units of pixels may be referred to as a "base image".

In this situation, the projection data generated from the count results obtained from the photon counting CT process includes information about energy of the X-rays that were attenuated as a result of passing through the patient P. For this reason, for example, the image reconstruction circuitry 36 is able to reconstruct X-ray CT image data corresponding to a specific energy component. Further, the image reconstruction circuitry 36 is able to reconstruct X-ray CT image data corresponding to each of a plurality of energy components, for example.

Further, for example, the image reconstruction circuitry 36 is configured to assign a color tone corresponding to an energy component to each of the pixels in each of a plurality of pieces of X-ray CT image data corresponding to the energy components and to generate image data in which the plurality of pieces of X-ray CT image data that are color-coded in accordance with the energy components are superimposed on one another. Further, for example, the image reconstruction circuitry 36 is capable of generating image data with which it is possible to identify substances by using the k-absorption edge unique to each substance. Other examples of image data generated by the image reconstruction circuitry 36 include monochrome X-ray image data, density image data, and effective atomic number image data, and the like.

Further, as an application of X-ray CT, a technique is known by which types, content amounts, density levels, and the like of substances contained in the patient P are discriminated, by using the fact that X-ray absorption characteristics are different among different substances. This technique is called substance identification. For example, the image reconstruction circuitry 36 is configured to perform a substance identification process on the projection data and to obtain substance identification information. Further, the image reconstruction circuitry 36 is configured to reconstruct a substance identification image by using the substance identification information resulting from the substance identification process.

To reconstruct a CT image, the image reconstruction circuitry 36 is able to use a full-scan reconstruction scheme and a half-scan reconstruction scheme. For example, when using the full-scan reconstruction scheme, the image reconstruction circuitry 36 requires projection data from the entire surrounding of the patient P corresponding to 360 degrees. In contrast, when using the half-scan reconstruction scheme, the image reconstruction circuitry 36 requires projection data corresponding to 180 degrees+a fan angle. In the following sections, to keep the explanation simple, it is assumed that the image reconstruction circuitry 36 uses the full-scan reconstruction scheme by which the reconstruction process is performed by using projection data from the entire surrounding of the patient P corresponding to 360 degrees.

The system control circuitry 38 is electric processing circuitry having a function of exercising overall control on the X-ray CT apparatus by controlling operations of the gantry 10, the couch 20, and the console 30. More specifically, the system control circuitry 38 controls a CT scan performed by the gantry 10, by controlling the scan control circuitry 33. Further, the system control circuitry 38 controls the image reconstruction process and the image generating process performed by the console 30, by controlling the pre-processing circuitry 34 and the image reconstruction circuitry 36. Further, the system control circuitry 38 exercises control so that the display 32 displays any of various types of image data stored in the image storage circuitry 37. For example, the image storage circuitry 37 is structured by using a NAND flash memory, an HDD, or the like and is configured to store therein various types of image data.

An overall configuration of the X-ray CT apparatus according to the first embodiment has thus been explained. The X-ray CT apparatus according to the first embodiment structured as described above is configured to reconstruct the X-ray CT image data by using the photon counting detector.

Figure 6:
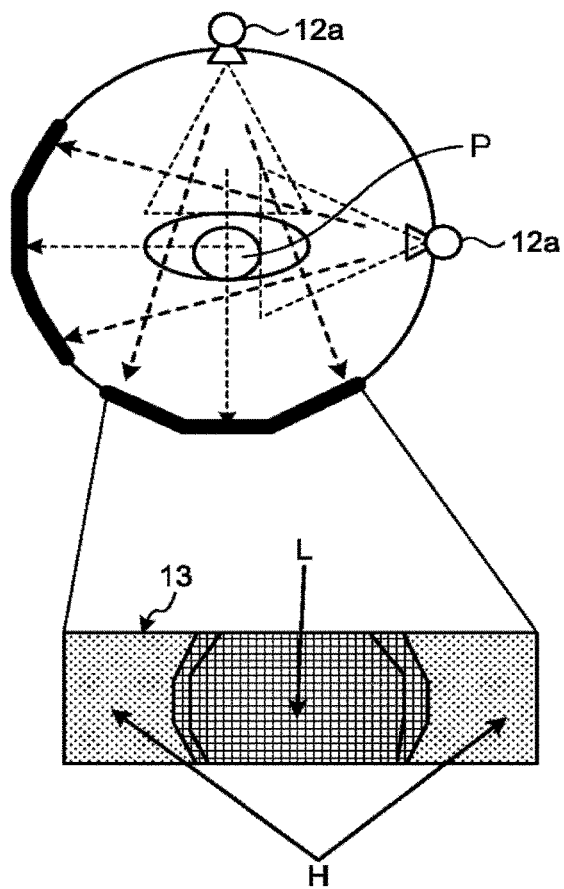
FIG. 6 is a drawing for explaining the quantity of photons becoming incident in accordance with positions of the detector.

Incidentally, while acquiring the count results, the ASICs 140 generate heat in accordance with the count rates thereof. Because the ASICs 140 are arranged in the vicinity of the detector 13, the heat generated by the ASICs 140 is easily transferred to the detector 13. In this situation when the detectors 13 in a large quantity are structured into an area detector, the quantity of photons becoming incident varies depending on positions of the detector 13. FIG. 6 is a drawing for explaining the quantity of photons becoming incident in accordance with positions of the detector 13. FIG. 6 illustrates the patient P as well as the X-ray tube 12a and the detector 13 rotating on the circular orbit centered on the patient P.

Cross-sections of the patient P are not circular but are oval. For this reason, as illustrated in FIG. 6, to periphery parts H of the detector 13, a larger quantity of photons becomes incident because a smaller quantity of photons pass through the patient P. In contrast, to a central part L, only a smaller quantity of photons becomes incident because a larger quantity of photons passes through the patient P. Accordingly, the ASICs 140 connected to the periphery parts H of the detector 13 tend to have higher count rates and generate more heat. On the contrary, the ASICs 140 connected to the central part L of the detector 13 tend to have lower count rates and generate less heat. In other words, in accordance with the positions in which the detection areas are arranged in the detector 13, the count rates vary among the ASICs 140. For this reason, the amount of generated heat transferred from the ASICs 140 varies among local sections of the detector 13.

Further, characteristics of the detector 13 have high dependency on temperature. A correspondence relationship between ambient temperature and dark count rate values is that, as the ambient temperature rises, the dark count rate also increases. Further, A correspondence relationship between ambient temperature and multiplication factors is that, as the ambient temperature rises, the multiplication factor decreases. For this reason, the heat generation of the ASICs 140 affects the characteristics of the detector 13. Accordingly, it is desirable to locally manage the temperature of the detector 13.

In view of the circumstances described above, the X-ray CT apparatus according to the first embodiment is configured to address local temperature changes in the detector 13 by performing a temperature controlling process. For example, the X-ray CT apparatus according to the first embodiment is configured to calculate an amount of generated heat (hereinafter "heat generation amount") for each of the detection areas of the detector 13. Further, the X-ray CT apparatus according to the first embodiment is configured to determine a control amount on the basis of the heat generation amount and to further control the temperature of each of the detection areas of the photon counting detector by using the determined control amount. The temperature controlling process performed in this manner by the X-ray CT apparatus is realized by the calculation circuitry 146 and the control circuitry 147 by employing the first correspondence information storage circuitry 148 and the second correspondence information storage circuitry 149. In the following sections, the calculation circuitry 146 and the control circuitry 147 according to the first embodiment will be explained in detail, with reference to FIGS. 7 to 10.

The first correspondence information storage circuitry 148 is structured by using a NAND flash memory or an HDD, for example, and is configured to store therein first correspondence information. FIG. 9 is a table illustrating an example of information stored in the first correspondence information according to the first embodiment. As illustrated in FIG. 9, the first correspondence information stores therein information in which "count rates" are kept in correspondence with "heat generation amounts". In this situation, the first correspondence information is generated by either measuring or conjecturing from a simulation, in advance, count rates in units of the views from the detection areas of the detector 13 output from the ASICs 140 and heat generation amounts of the ASICs 140.

In this situation, the following explanation is based on the assumption that the count rates in units of the views are each calculated as an average value of the detection signals from the two or more detecting elements included in each of the detection areas. However, the count rates each do not necessarily have to be an average value. For example, the count rates may each be a maximum value or a minimum value among the detection signals from the two or more detecting elements.

The "count rates" in the first correspondence information indicate count results corresponding to a view. For example, as the "count rates", pieces of information such as "C<C1" indicating that the count rate is lower than C1 and "C1≤C<C2" indicating that the count rate is equal to or higher than C1 but lower than C2 are stored. Further, the "heat generation amounts" in the first correspondence information indicate heat generation amounts of the ASICs 140 based on the count rates. For example, as the "heat generation amounts", pieces of information such as "Q1", "Q2" and the like are stored.

In one example, the first correspondence information illustrated in FIG. 9 indicates that the heat generation amount of the ASICs 140 is Q1 when the count rate is lower than C1 and that the heat generation amount of the ASICs 140 is Q2 when the count rate is equal to or higher than C1 but lower than C2.

Figures 10, 11:
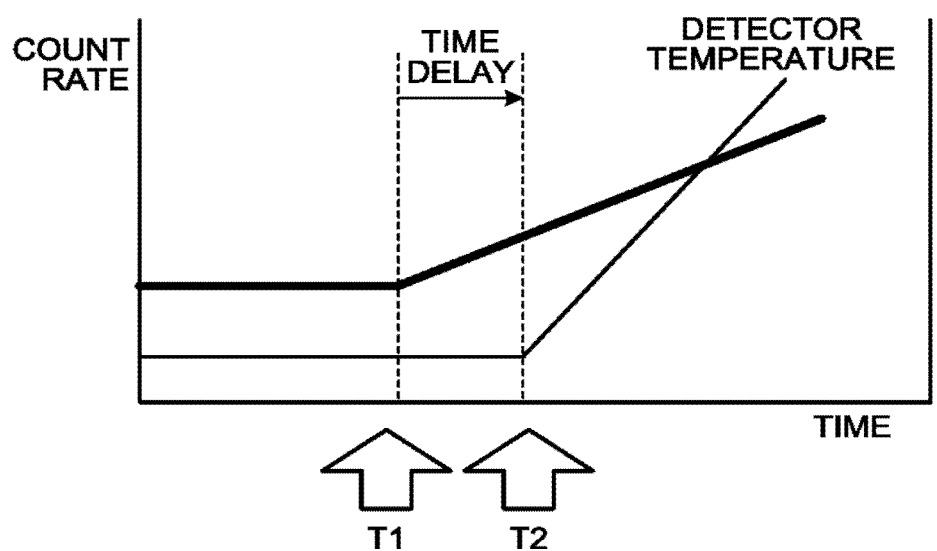
FIG. 10 is a table illustrating an example of information stored in second correspondence information according to the first embodiment.
FIG. 11 is a chart for explaining the first embodiment.

The second correspondence information storage circuitry 149 is structured by using a NAND flash memory or an HDD, for example, and is configured to store therein second correspondence information. FIG. 10 is a table illustrating an example of information stored in the second correspondence information according to the first embodiment. As illustrated in FIG. 10, the second correspondence information stores therein information in which "detection area IDs", "heat generation amounts", and "control amounts" are kept in correspondence with one another. The second correspondence information is generated by either conjecturing or measuring, in advance, temperature changes caused on the detector 13 by heat generation amounts of the ASICs 140.

The "detection area IDs" in the second correspondence information indicate identifiers used for identifying the positions of the detection areas in the detector 13, which is of a photon counting type. For example, pieces of information such as "A1", "A2", and the like are stored as the "detection area IDs".

The "heat generation amounts" in the second correspondence information are the same as the "heat generation amounts" in the first correspondence information. Further, the "control amounts" in the second correspondence information indicate control amounts for the temperature controllers 17 based on the heat generation amounts. For example, pieces of information such as "R1", "R2", and the like are stored as the "control amounts".

In one example, the second correspondence information illustrated in FIG. 10 indicates that the control amount for the temperature controller 17 is R1 when the heat generation amount of the detection area identified with the detection area identifier "A1" is Q1 and that the control amount for the temperature controller 17 is R2 when the heat generation amount of the detection area identified with the detection area identifier "A1" is Q2.

Figure 7:
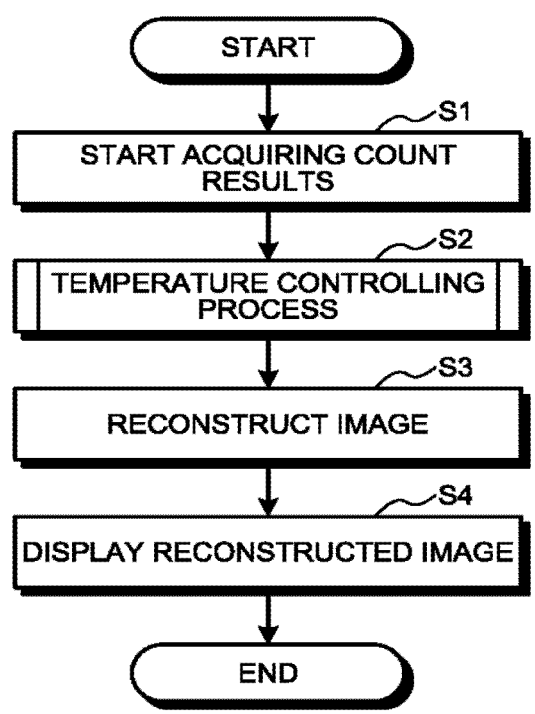
FIG. 7 is a flowchart illustrating a processing procedure performed by the X-ray CT apparatus according to the first embodiment to reconstruct an X-ray CT image.

FIG. 7 is a flowchart illustrating a processing procedure performed by the X-ray CT apparatus according to the first embodiment to reconstruct an X-ray CT image. For example, the processes illustrated in FIG. 7 are performed when the input interface 31 receives, from the operator, an instruction that a main image taking process should be performed, and the received instruction is transferred to the system control circuitry 38. Step S1 in FIG. 7 is a step realized by the scan control circuitry 33. At step S1, the scan control circuitry 33 causes the data acquisition circuitry 14 to start a count result acquiring process, by controlling the X-ray tube 12a to emit X-rays. Step S2 is a step realized by the calculation circuitry 146 and the control circuitry 147. At step S2, the calculation circuitry 146 and the control circuitry 147 perform the temperature controlling process. Details of step S2 will be explained later with reference to FIG. 8.

Step S3 is a step realized by the image reconstruction circuitry 36. At step S3, the image reconstruction circuitry 36 reconstructs X-ray CT image data on the basis of the acquired count results. In other words, the image reconstruction circuitry 36 reconstructs the image by using projection data based on the acquired detection signals. Step S4 is a step realized by the system control circuitry 38. At step S4, the system control circuitry 38 causes the display 32 to display the reconstructed X-ray CT image.

FIG. 8 is a flowchart illustrating a procedure performed by the X-ray CT apparatus according to the first embodiment to perform a temperature controlling process. The processing procedure illustrated in FIG. 8 corresponds to the process at step S2 in FIG. 7. Steps S101 through S103 are steps realized by the calculation circuitry 146. At step S101, the calculation circuitry 146 judges whether or not a view trigger signal has been received. When determining that a view trigger signal has been received (step S101: Yes), the calculation circuitry 146 proceeds to step S102. On the contrary, when determining that no view trigger signal has been received (step S101: No), the calculation circuitry 146 repeatedly performs the judging process at step S101.

At step S102, the calculation circuitry 146 obtains a count rate for each of the detection areas. For example, for each of the views, the calculation circuitry 146 obtains count results of the ASICs 140 in units of the detection areas. As the count rates in units of the views, for example, the calculation circuitry 146 obtains an average value of the detection signals from the two or more detecting elements included in each of the detection areas. Alternatively, as the count rates in units of the views, the calculation circuitry 146 may obtain, for example, either a maximum value or a minimum value among the detection signals from the two or more detecting elements included in each of the detection areas.

Further, at step S103, the calculation circuitry 146 calculates a heat generation amount for each of the detection areas in the detector 13. For example, by using the first correspondence information illustrated in FIG. 9, the calculation circuitry 146 identifies, for each of the views, heat generation amounts corresponding to the count rates obtained at step S102, in units of the detection areas.

In one example, by using the first correspondence information illustrated in FIG. 9, the calculation circuitry 146 identifies that the heat generation amount of the ASICs 140 is Q1 when the count rate is lower than C1 and identifies that the heat generation amount of the ASICs 140 is Q2 when the count rate is equal to or higher than C1 but lower than C2. In other words, the calculation circuitry 146 calculates the heat generation amount for each of the detection areas, by using the count results based on the detection signals from the detecting elements in each of the detection areas. In this manner, the calculation circuitry 146 calculates the heat generation amount for each of the detection areas, on the basis of the count rates based on the detection signals. In other words, the calculation circuitry 146 calculates the heat generation amount for each of the detection areas, on the basis of the detection signals corresponding to the incident photons detected in each of the detection areas.

Steps S104 through S106 are steps realized by the control circuitry 147. At step S104, the control circuitry 147 determines control amounts on the basis of the heat generation amounts. For example, by using the second correspondence information illustrated in FIG. 10, the control circuitry 147 identifies, for each of the views, control amounts corresponding to the heat generation amounts identified at step S103, in units of the detection areas. In other words, the control circuitry 147 determines the control amount on the basis of the heat generation amount for each of the detection areas and further controls the temperature in each of the detection areas by using the determined control amount.

In this situation, in the vicinity of the DAS, an air-cooling fan is provided to control the temperature of the entire DAS by discharging the heat of the DAS. In this situation, when only one air-cooling fan is provided, the heat discharging efficiency may be different between positions near the air-cooling fan and positions distant from the air-cooling fan. When the heat discharging efficiency is different between the ASICs 140 positioned in a central part of the detector 13 and the ASICs 140 positioned in a periphery part of the detector 13 depending on the number of air-cooling fans provided in the vicinity of the DAS, required control amounts will be different between the central part and the periphery part of the detector 13, even though the heat generation amounts of the ASIC 140 are the same. Accordingly, in the following sections, an example will be explained in which the number of air-cooling fans provided in the vicinity of the DAS is one, and the heat discharging efficiency varies among the ASICs 140.

In that situation, the control circuitry 147 determines a control amount corresponding to the position of each of the detection areas in the detector 13 of a photon counting type. In one example, by using the second correspondence information illustrated in FIG. 10, the control circuitry 147 identifies that the control amount for the temperature controller 17 is R1 when the heat generation amount of the detection area identified with the detection area identifier "A1" is Q1 and identifies that the control amount for the temperature controller 17 is R2 when the heat generation amount of the detection area identified with the detection area identifier "A1" is Q2. Further, by using the second correspondence information illustrated in FIG. 10, the control circuitry 147 identifies that the control amount for the temperature controller 17 is R2 when the heat generation amount of the detection area identified with the detection area identifier "A2" is Q1.

In other words, the control circuitry 147 determines the control amounts on the basis of the heat generation amounts.

At step S105, the control circuitry 147 controls the temperature controllers 17. For example, the control circuitry 147 instructs the temperature controllers 17 to set the control amounts identified at step S104. In other words, the control circuitry 147 controls the temperature of each of the detection areas in the detector 13 by using the determined control amounts. In this situation, for each of the views, the control circuitry 147 instructs each of temperature controllers 17 with a control amount.

At step S106, the control circuitry 147 judges whether or not information indicating that the image taking process should be ended is received. When having determined that information indicating that the image taking process should be ended is received (step S106: Yes), the control circuitry 147 ends the temperature controlling process. On the contrary, when having determined that no information indicating that the image taking process should be ended is received (step S106: No), the control circuitry 147 proceeds to step S101.

As explained above, according to the first embodiment, the control amounts to compensate the temperature increases in the detection areas of the detector 13 are determined on the basis of the output values (the count rates) of the ASICs 140 during the scan so as to operate the temperature controllers 17. In other words, according to the first embodiment, the heat generation amount is calculated for each of the detection areas in the photon counting detector, so that the temperature of each of the detection areas in the photon counting detector is controlled by using the control amounts determined on the basis of the heat generation amounts. For example, according to the first embodiment, one temperature controller 17 is provided for each of the detection areas. With this arrangement, it is possible to make smaller the scale of the controlled regions, compared to the situation where the temperature changes are addressed for the entire detector 13. By making the scale of the controlled regions smaller in this manner, it is possible to predict temperature changes more easily. As a result, according to the first embodiment, it is possible to address the local temperature changes in the detector 13.

Incidentally, as an alternative method for addressing the temperature changes, it is also possible to combine a temperature measuring process using temperature sensors with temperature controllers (coolers/heaters) so as to control the temperature controllers with feedback from the temperature sensors. In that situation, the temperature sensors would be provided in the vicinity of the detector 13 so as to control the temperature of the detector 13 on the basis of output values from the temperature sensors. According to this alternative method, however, because the large number of temperature sensors would be placed on the detector 13, the installation and the signal lines for the temperature sensors would increase. For this reason, the alternative method would exhibit a difficulty related to the installation.

In contrast, according to the first embodiment, the local temperature changes in the detector 13 are addressed without using any temperature sensor. In other words, according to the first embodiment, there is no need to arrange a large number of temperature sensors. For this reason, according to the first embodiment, it is possible to address the local temperature changes in the detector 13, while avoiding the difficulty related to the installation.

Further, according to the alternative method, it would be possible to start exercising control only after at least one of the temperature sensors detects an increase in the temperature. In that situation, the control amounts would easily overshoot (or undershoot). In contrast, according to the first embodiment, the heat generation amount for each of the detection areas is calculated by using the count results based on the detection signals from the detecting elements in the detection area. With this arrangement, according to the first embodiment, it is possible to enhance followability of the detector 13 for the temperature changes. FIG. 11 is a chart for explaining the first embodiment.

In FIG. 11, the horizontal axis expresses time, whereas the vertical axis expresses the count rate and the temperature of the detector 13. In this situation, for example, according to the alternative method, the temperature is measured by the temperature sensors, so that the control of the temperature controllers 17 would start at a time T2 when the temperature of the detector 13 starts rising. In other words, according to the alternative method, the control of the temperature controllers 17 would start after at least one of the temperature sensors detects a rise in the temperature. In contrast, according to the first embodiment, the control of the temperature controllers 17 starts at a time T1 when the count rate starts increasing. In other words, according to the first embodiment, the control of the temperature controllers 17 starts before the temperature sensors detect a rise in the temperature. With this arrangement, when the temperature controlling method according to the first embodiment is used, it is possible to start the control of the temperature controllers 17 earlier than the start of the control of the temperature controllers 17 according to the alternative method, by a time period $\Delta T$ (T2−T1). As a result, according to the first embodiment, it is possible to prevent the temperature of the detector 13 from rising more efficiently, before the temperature of the detector 13 starts rising. In other words, according to the first embodiment, it is possible to prevent the control amounts from overshooting (or undershooting).

Further, it is also acceptable to configure the detector 13 to have a thermal insulation structure between each of the detection areas. For example, a layer having a high thermal conductivity may be interposed between the ASICs 140 and the detector 13, so that heat does not concentrate in certain locations within the detection areas. In that situation, a ground layer or a power source layer for the circuit may be used as the layer having a high thermal conductivity. Using such a thermal insulation structure is effective when the detection areas are structured as modules.

Second Embodiment

Figure 12:
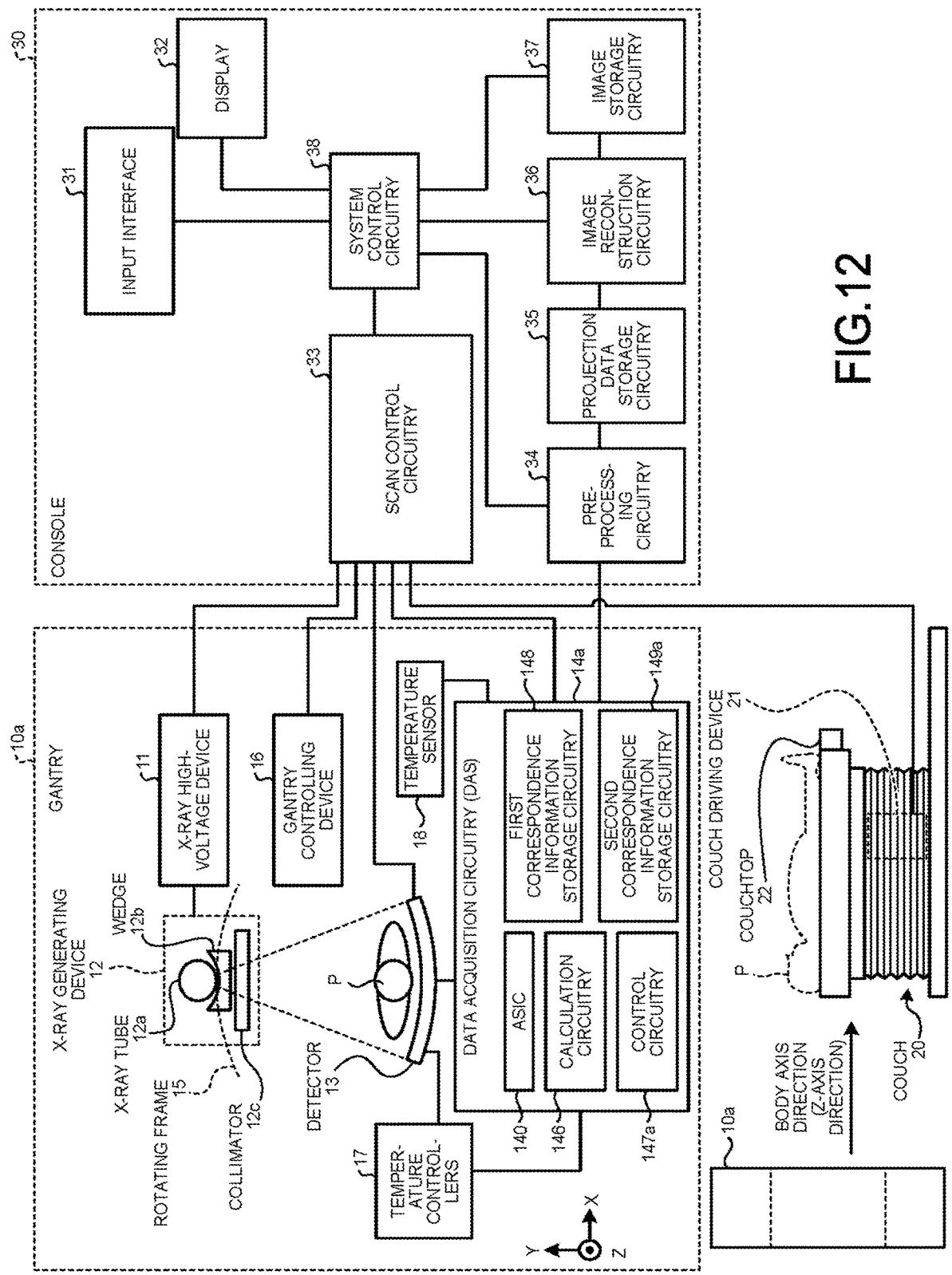
FIG. 12 is a block diagram illustrating an exemplary configuration of an X-ray CT apparatus according to a second embodiment.

In a second embodiment, an example will be explained in which a temperature controlling process is performed by further taking into account the temperature in the vicinity of the detector 13. FIG. 12 is a block diagram illustrating an exemplary configuration of an X-ray CT apparatus according to the second embodiment. In FIG. 12, some of the constituent elements having the same functions as those illustrated in FIG. 1 are referred to by using the same reference characters, and the detailed explanations thereof will be omitted. As illustrated in FIG. 12, the X-ray CT apparatus according to the second embodiment includes a gantry 10*a*, the couch 20, and the console 30.

The gantry 10*a* has a similar configuration to that of the gantry 10 illustrated in FIG. 1, except that a temperature sensor 18 is further provided and that the configuration of data acquisition circuitry 14*a* is partially different from the configuration of the data acquisition circuitry 14 according to the first embodiment. Accordingly, in the following sections, only a configuration of the temperature sensor 18 according to the second embodiment and a configuration of the data acquisition circuitry 14*a* according to the second embodiment will be explained.

The temperature sensor 18 is provided in the vicinity of the detector 13 and is configured to detect the temperature in the vicinity of the detector 13. The data acquisition circuitry 14*a* includes the ASICs 140, the calculation circuitry 146, control circuitry 147a, the first correspondence information storage circuitry 148, and second correspondence information storage circuitry 149a. The configurations of the ASICs 140, the calculation circuitry 146, and the first correspondence information storage circuitry 148 included in the data acquisition circuitry 14a are the same as the configurations of the ASICs 140, the calculation circuitry 146, and the first correspondence information storage circuitry 148 included in the data acquisition circuitry 14.

The second correspondence information storage circuitry 149a is structured by using a NAND flash memory or an HDD, for example, and is configured to store therein second correspondence information. FIG. 14 is a table illustrating an example of information stored in the second correspondence information according to the second embodiment. As illustrated in FIG. 14, the second correspondence information stores therein information in which "detection area IDs", "heat generation amounts", "external temperatures", and "control amounts" are kept in correspondence with one another. The "detection area IDs" in the second correspondence information are the same as the "detection area IDs" in the second correspondence information illustrated in FIG. 10. The "heat generation amounts" in the second correspondence information are the same as the "heat generation amounts" in the first correspondence information illustrated in FIG. 9. The second correspondence information is generated by either conjecturing or measuring, in advance, temperature changes caused on the detector 13 by the heat generation amounts of the ASICs 140, while taking into consideration an impact made by a difference in the external temperature.

Further, the "external temperatures" in the second correspondence information each indicate a temperature in the vicinity of the detector 13 obtained from the temperature sensor 18. For example, as the "external temperatures", pieces of information such as "T<T1" indicating that the temperature in the vicinity of the detector 13 is lower than T1, "T1≤T<T2" indicating that the temperature in the vicinity of the detector 13 is equal to or higher than T1 but lower than T2, and the like are stored.

Further, the "control amounts" in the second correspondence information indicate control amounts for the temperature controller 17 each based on a heat generation amount and a temperature in the vicinity of the detector 13. For example, as the "control amounts", pieces of information such as "R11", "R12" and the like are stored.

In one example, the second correspondence information illustrated in FIG. 14 indicates that the control amount for the temperature controller 17 is R12 when the heat generation amount of the detection area identified with the detection area identifier "A1" is Q1, while the temperature in the vicinity of the detector 13 is equal to or higher than T1 but lower than T2 and indicates that the control amount for the temperature controller 17 is R23 when the heat generation amount of the detection area identified with the detection area identifier "A1" is Q2, while the temperature in the vicinity of the detector 13 is equal to or higher than T2.

The control circuitry 147a is configured to determine a control amount by using the heat generation amount and the temperature that was measured in the vicinity of the detector 13, which is of a photon counting type, and was obtained from the temperature sensor 18. Further, by using the determined control amount, the control circuitry 147a is configured to control the temperature for each of the detection areas in the detector 13.

Figure 13:
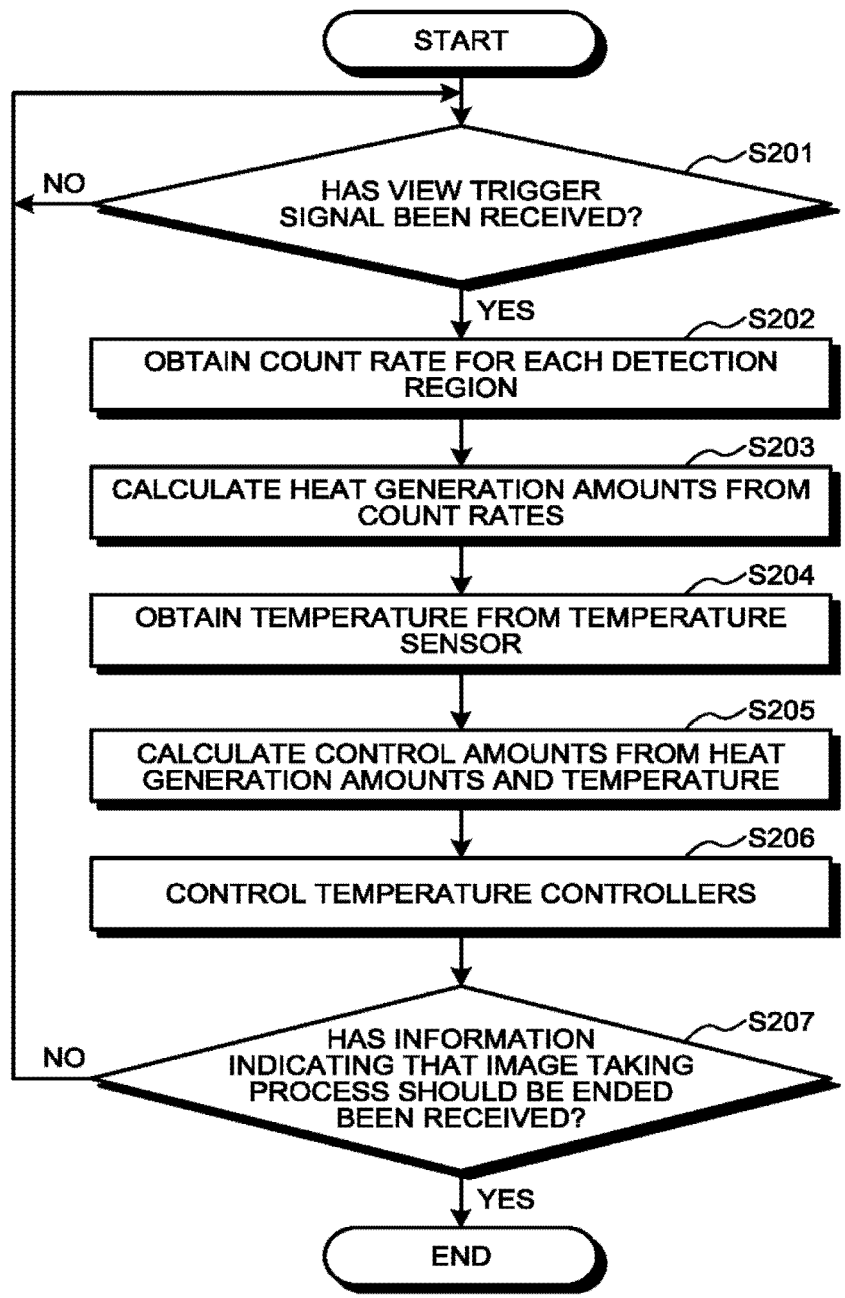
FIG. 13 is a flowchart illustrating a procedure performed by the X-ray CT apparatus according to the second embodiment to perform a temperature controlling process.

Next, a processing procedure performed by the X-ray CT apparatus according to the second embodiment will be explained. The processing procedure performed by the X-ray CT apparatus according to the second embodiment to reconstruct an X-ray CT image is similar to the processing procedure illustrated in FIG. 7 performed by the X-ray CT apparatus according to the first embodiment to reconstruct an X-ray CT image, except that details of the process at step S2 are different. Accordingly, in the second embodiment only a procedure in the temperature controlling process will be explained. FIG. 13 is a flowchart illustrating the procedure performed by the X-ray CT apparatus according to the second embodiment to perform the temperature controlling process.

The processing procedure illustrated in FIG. 13 corresponds to the process at step S2 in FIG. 7. Steps S201 through S203 are steps realized by the calculation circuitry 146. The processes at steps S201 through S203 correspond to the processes at steps S101 through S103 in FIG. 8.

Steps S204 through S207 are steps realized by the control circuitry 147a. At step S204, the control circuitry 147a obtains a temperature from the temperature sensor 18. At step S205, the control circuitry 147a calculates control amounts from the heat generation amounts and the temperature. For example, by using the second correspondence information illustrated in FIG. 14, the control circuitry 147a identifies, for each of the views, control amounts corresponding to the heat generation amounts identified at step S203 and to the temperature obtained at step S204, in units of the detection areas. In other words, the control circuitry 147a determines the control amounts by using the heat generation amount for each of the detection areas and the temperature that was measured in the vicinity of the detector 13, which is of a photon counting type, and was obtained from the temperature sensor 18.

In one example, by using the second correspondence information illustrated in FIG. 14, the control circuitry 147a identifies that the control amount for the temperature controller 17 is R12 when the heat generation amount of the detection area identified with the detection area identifier "A1" is Q1, while the temperature in the vicinity of the detector 13 is equal to or higher than T1 but lower than T2 and identifies that the control amount for the temperature controller 17 is R23 when the heat generation amount of the detection area identified with the detection area identifier "A1" is Q2, while the temperature in the vicinity of the detector 13 is equal to or higher than T2. In other words, the control circuitry 147a determines the control amounts by using the heat generation amounts and the temperature in the vicinity of the detector 13 obtained from the temperature sensor 18.

At step S206, the control circuitry 147a controls the temperature controllers 17. For example, the control circuitry 147a instructs the temperature controllers 17 to set the control amounts identified at step S205. In this situation, for each of the views, the control circuitry 147a instructs each of the temperature controllers 17 with a control amount.

At step S207, the control circuitry 147a judges whether or not information indicating that the image taking process should be ended is received. When having determined that information indicating that the image taking process should be ended is received (step S207: Yes), the control circuitry 147a ends the temperature controlling process. On the contrary, when having determined that no information indicating that the image taking process should be ended is received (step S207: No), the control circuitry 147a proceeds to step S201.

As explained above, according to the second embodiment, the X-ray CT apparatus is configured to determine the control amounts to compensate the temperature increases in the detection areas of the detector 13 on the basis of the output values (the count rates) of the ASICs 140 during the scan and the temperature in the vicinity of the detector 13 so as to operate the temperature controllers 17. In other words, according to the second embodiment, the temperature controlling process is performed by further taking the temperature in the vicinity of the detector 13 into account. As a result, according to the second embodiment, it is possible to more accurately address the local temperature changes in the detector 13.

Third Embodiment

Figure 15:
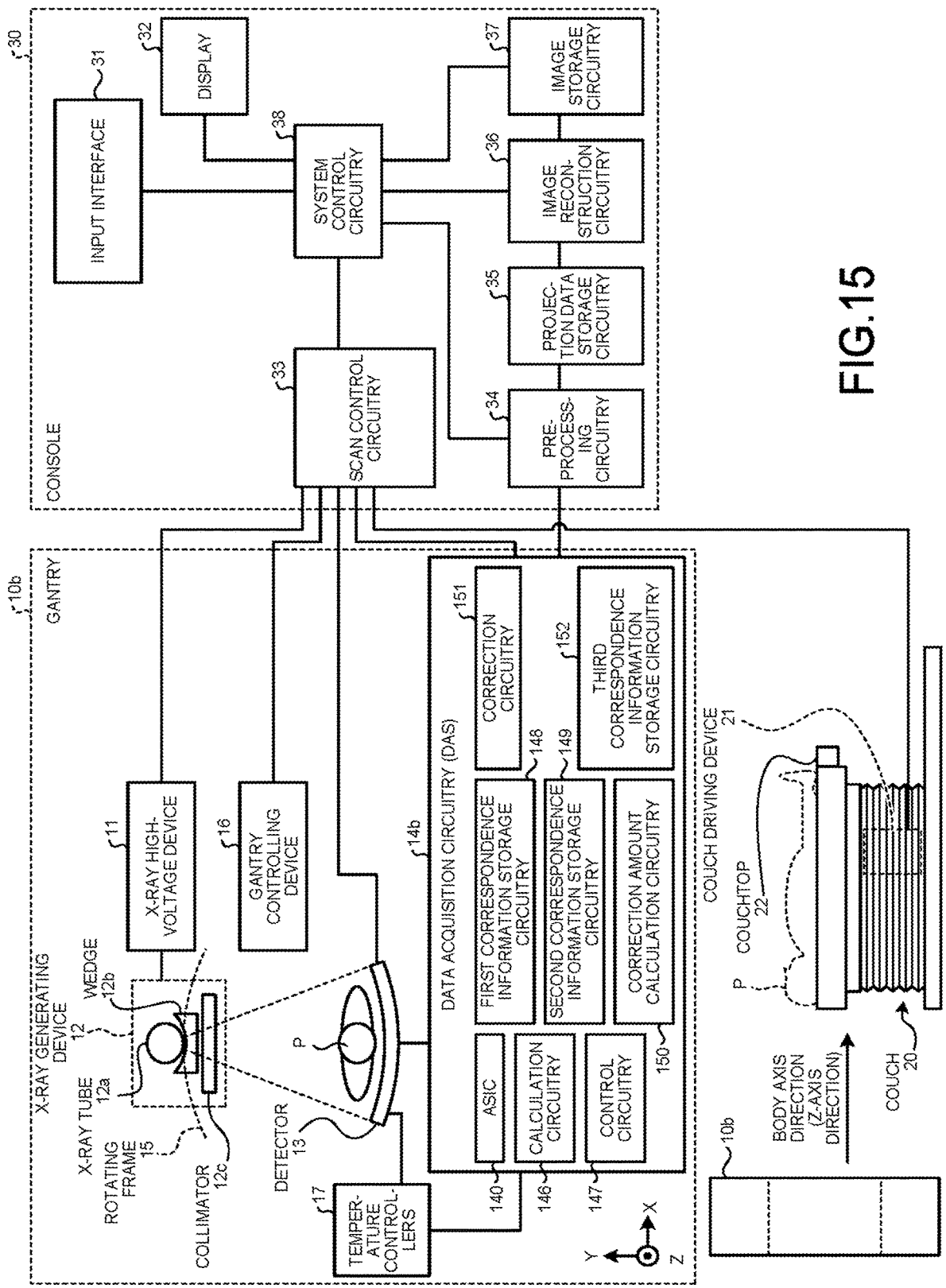
FIG. 15 is a block diagram illustrating an exemplary configuration of an X-ray CT apparatus according to a third embodiment.

In a third embodiment, an example will be explained in which an image is reconstructed after correcting an impact made on characteristics of the detector 13 by temperature changes in the detector 13. FIG. 15 is a block diagram illustrating an exemplary configuration of an X-ray CT apparatus according to the third embodiment. In FIG. 15, some of the constituent elements having the same functions as those illustrated in FIG. 1 are referred to by using the same reference characters, and the detailed explanations thereof will be omitted. As illustrated in FIG. 15, the X-ray CT apparatus according to the third embodiment includes the gantry 10b, the couch 20, and the console 30.

The configuration of the gantry 10b is similar to that of the gantry 10 illustrated in FIG. 1, except that the configuration of data acquisition circuitry 14b is partially different from the configuration of the data acquisition circuitry 14 according to the first embodiment. Accordingly, in the following sections, only the configuration of the data acquisition circuitry 14b according to the third embodiment will be explained.

The data acquisition circuitry 14b includes the ASICs 140, the calculation circuitry 146, the control circuitry 147, the first correspondence information storage circuitry 148, the second correspondence information storage circuitry 149, correction amount calculation circuitry 150, correction circuitry 151, and third correspondence information storage circuitry 152. The configurations of the ASICs 140, the calculation circuitry 146, the control circuitry 147, the first correspondence information storage circuitry 148, and the second correspondence information storage circuitry 149 included in the data acquisition circuitry 14b are the same as the configurations of the ASICs 140, the calculation circuitry 146, the control circuitry 147, the first correspondence information storage circuitry 148, and the second correspondence information storage circuitry 149 included in the data acquisition circuitry 14.

The third correspondence information storage circuitry 152 is structured by using a NAND flash memory or an HDD, for example, and is configured to store therein third correspondence information. FIG. 18 is a table illustrating an example of information stored in the third correspondence information according to the third embodiment. As illustrated in FIG. 18, the third correspondence information stores therein information in which "change amounts in the count rate", "control amounts", and "correction amounts" are kept in correspondence with one another. The third correspondence information is generated by either conjecturing or measuring, in advance, temperature changes caused on the detector 13 by heat generation amounts of the ASICs 140 and changes in characteristics of the detector 13 caused by the temperature changes.

Each of the "change amounts in the count rate" in the third correspondence information indicates the difference between the count result in the current view and the count result in an immediately preceding view. For example, as the "change amounts in the count rate", pieces of information such as "$\Delta C<C11$" indicating that the difference is smaller than C11, "$C11 \leq \Delta C<C12$" indicating that the difference is equal to or larger than C11 but smaller than C12, and the like are stored.

Further, each of the "control amounts" in the third correspondence information indicates a control amount for the temperature controller 17 identified on the basis of the count rate corresponding to the immediately preceding view. For example, as the "control amounts", pieces of information such as "R111", "R112", and the like are stored.

Further, each of the "correction amounts" in the third correspondence information indicates a correction amount for the count result based on a change amount in the count rate. For example, as the "correction amounts", pieces of information such as "$\alpha 1$", "$\alpha 2$", and the like are stored.

In one example, the third correspondence information illustrated in FIG. 18 indicates that the correction amount is $\alpha 1$ when the change amount in the count rate is smaller than C11, while the control amount for the temperature controller 17 is R111 and indicates that the correction amount is $\alpha 3$ when the change amount in the count rate is smaller than C11, while the control amount for the temperature controller 17 is R113.

The correction amount calculation circuitry 150 is configured to calculate a correction amount corresponding to a temperature change in the detector 13. The correction circuitry 151 is configured to correct the detection signals output by the detector 13 by using the correction amounts.

Figure 16:
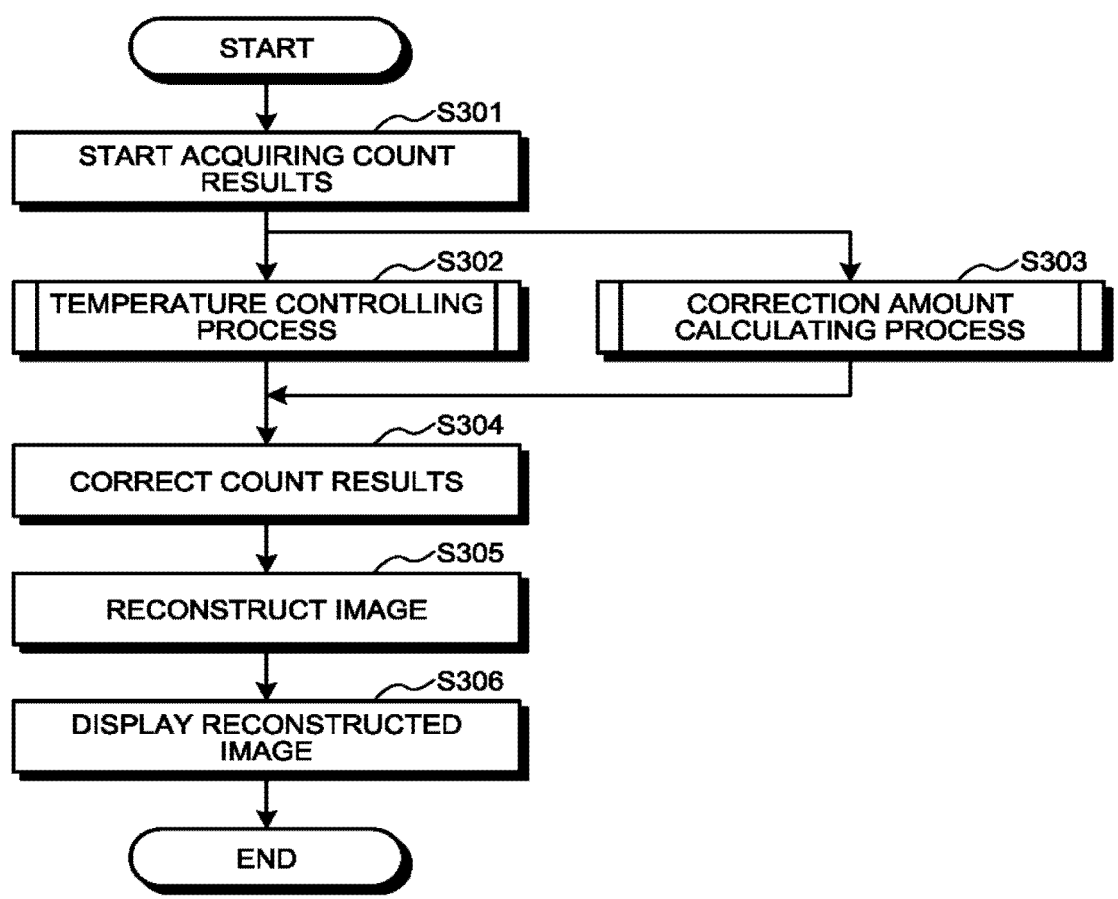
FIG. 16 is a flowchart illustrating a processing procedure performed by the X-ray CT apparatus according to the third embodiment to reconstruct an X-ray CT image.

Next, a processing procedure performed by the X-ray CT apparatus according to the third embodiment to reconstruct an X-ray CT image will be explained. FIG. 16 is a flowchart illustrating the processing procedure performed by the X-ray CT apparatus according to the third embodiment to reconstruct the X-ray CT image. Step S301 in FIG. 16 is a step realized by the scan control circuitry 33. At step S301, the scan control circuitry 33 causes the data acquisition circuitry 14b to start a count result acquiring process, by controlling the X-ray tube 12a to emit X-rays.

Subsequent to the process at step S301, steps S302 and S303 are performed parallel to each other. Step S302 is a step realized by the calculation circuitry 146 and the control circuitry 147. At step S302, the calculation circuitry 146 and the control circuitry 147 perform a temperature controlling process. The processing procedure performed at step S302 is the same as the processing procedure explained with reference to FIG. 8.

Step S303 is a step realized by the correction amount calculation circuitry 150. At step S303, the correction amount calculation circuitry 150 performs a correction amount calculating process. Details of step S303 will be explained, with reference to FIG. 17.

Figure 17:
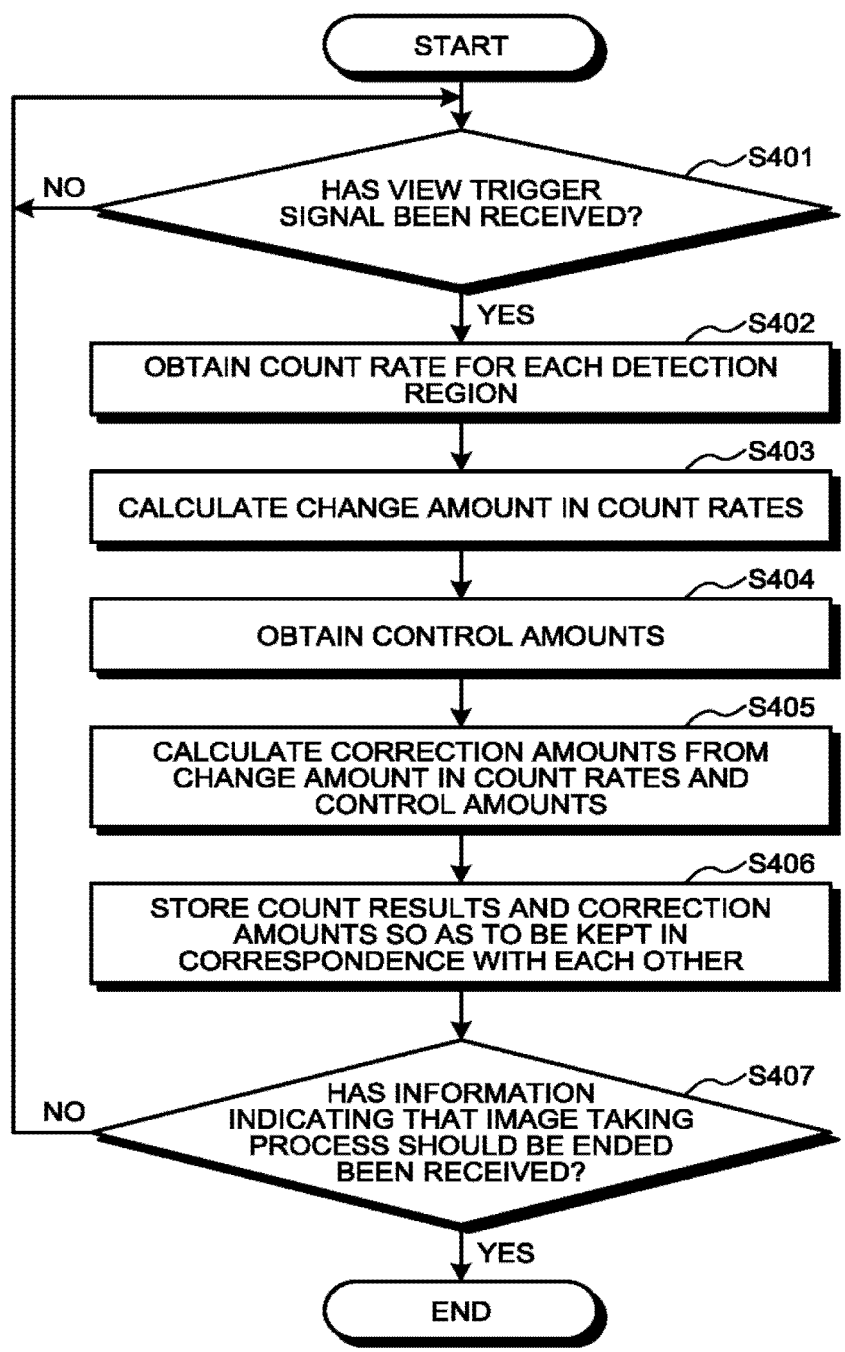
FIG. 17 is a flowchart illustrating a procedure performed by the X-ray CT apparatus according to the third embodiment to perform a correction amount calculating process.

FIG. 17 is a flowchart illustrating a procedure performed by the X-ray CT apparatus according to the third embodiment to perform the correction amount calculating process. The processing procedure illustrated in FIG. 17 corresponds to the process at step S303 in FIG. 16. Steps S401 through S407 are steps realized by the correction amount calculation circuitry 150.

At step S401, the correction amount calculation circuitry 150 judges whether or not a view trigger signal has been received. When determining that a view trigger signal has been received (step S401: Yes), the correction amount calculation circuitry 150 proceeds to step S402. On the contrary, when determining that no view trigger signal has been received (step S401: No), the correction amount calculation circuitry 150 repeatedly performs the judging process as at step S401.

At step S402, the correction amount calculation circuitry 150 obtains a count rate for each of the detection areas. For example, for each of the views, the correction amount calculation circuitry 150 obtains count results of the ASICs 140 in units of the detection areas. At step S403, the correction amount calculation circuitry 150 calculates a change amount in the count rates. For example, the correction amount calculation circuitry 150 calculates the difference between the count rate obtained in the current view and the count rate obtained in the immediately preceding view.

At step S404, the correction amount calculation circuitry 150 obtains control amounts. For example, the correction amount calculation circuitry 150 obtains a control amount for the immediately preceding view on the basis of the count rate in the immediately preceding view, by referring to the first correspondence information and the second correspondence information.

At step S405, the correction amount calculation circuitry 150 calculates correction amounts on the basis of the change amount in the count rates and the control amounts. For example, the correction amount calculation circuitry 150 calculates the correction amounts by using the change amount in the count rate calculated at step S403, the control amounts obtained at step S404, and the third correspondence information illustrated in FIG. 18. In other words, the correction amount calculation circuitry 150 calculates the correction amounts by conjecturing a temperature change in the detector 13, on the basis of a history of the count results corresponding to the views based on the detection signals from the detecting elements in each of the detection areas and the control amounts.

In one example, by using the third correspondence information illustrated in FIG. 18, the correction amount calculation circuitry 150 identifies that the correction amount is α1 when the change amount in the count rate is smaller than C11, while the control amount for the temperature controller 17 is R111 and identifies that the correction amount is α3 when the change amount in the count rate is smaller than C11, while the control amount for the temperature controller 17 is R113. In one example, the correction amount calculation circuitry 150 estimates, as a correction value, a dark current value on the basis of the count rate corresponding to each of the views. Alternatively, the correction amount calculation circuitry 150 may estimate, as the correction value, a gain value of pixels on the basis of the count rate corresponding to each of the views.

Returning to the description of FIG. 17, at step S406, the correction amount calculation circuitry 150 stores the current view number, the count results for the current view, and the correction amounts calculated at step S405 so as to be kept in correspondence with one another.

At step S407, the correction amount calculation circuitry 150 judges whether or not information indicating that the image taking process should be ended is received. When having determined that information indicating that the image taking process should be ended is received (step S407: Yes), the correction amount calculation circuitry 150 ends the correction amount calculating process. On the contrary, when having determined that no information indicating that the image taking process should be ended is received (step S407: No), the correction amount calculation circuitry 150 proceeds to step S401.

Returning to the description of FIG. 16, step S304 is a step realized by the correction circuitry 151. At step S304, the correction circuitry 151 corrects the count results by using the correction amounts calculated at step S303. For example, the correction circuitry 151 corrects the count results, by using the correction amounts stored in correspondence with the count results. In one example, the correction circuitry 151 corrects the count results, by using a dark current value estimated on the basis of the count rate corresponding to each of the views. Alternatively, the correction circuitry 151 may correct the count results, by using a gain value of pixels estimated on the basis of the count rate corresponding to each of the views.

Step S305 is a step realized by the image reconstruction circuitry 36. At step S305, the image reconstruction circuitry 36 reconstructs X-ray CT image data on the basis of the count results corrected at step S304. In other words, the image reconstruction circuitry 36 reconstructs an image by using projection data based on the corrected detection signals. Step S306 is a step realized by the system control circuitry 38. At step S306, the system control circuitry 38 causes the display 32 to display the reconstructed X-ray CT image.

In the third embodiment, for each of the views, the temperature change in the detector 13 is estimated on the basis of the history of the count rates and further calculates the change in the characteristics corresponding to the estimated temperature change as the correction amounts. In other words, according to the third embodiment, the count results are further corrected while addressing the local temperature changes in the detector 13. As a result, according to the third embodiment, it is possible to reconstruct a more accurate image. Further, although the example is explained in the third embodiment in which the temperature change is estimated on the basis of the history including the current view and the immediately preceding view, possible embodiments are not limited to this example. For instance, it is also acceptable to estimate a temperature change on the basis of a history including the current view, the immediately preceding view, two views ago, and three views ago, for example.

A Modification Example of the Third Embodiment

In the third embodiment above, the example is explained in which the correction amount calculation circuitry 150 calculates the correction amounts by conjecturing the temperature change in the detector 13 on the basis of the control amounts and the history of the count results for each of the views based on the signals from the detecting elements in each of the detection areas; however, possible embodiments are not limited to this example. For instance, when the X-ray CT apparatus includes a temperature sensor, it is also acceptable to detect a temperature change by using the temperature sensor, to conjecture a change in the characteristics of the detector on the basis of the detected temperature change, and to further calculate a correction value.

More specifically, in a modification example of the third embodiment, information that keeps "temperature changes" and "correction amounts" in correspondence with one another is stored as the third correspondence information. Each of the temperature changes indicates, for example, a difference between a temperature detected by the temperature sensor in the current view and a temperature detected by the temperature sensor in the immediately preceding view. In that situation, the correction amount calculation circuitry 150 calculates a correction amount corresponding to the temperature change. After that, the correction circuitry 151 corrects the count results by using the correction amounts.

In this manner, the correction amount calculation circuitry 150 conjectures the temperature change in the detector 13 on the basis of the temperature in the vicinity of the detector 13 obtained from the temperature sensor and further calculates the correction amounts. In other words, in the modification example of the third embodiment, the count results are further corrected while addressing the local temperature changes in the detector 13. As a result, according to the modification example of the third embodiment, it is possible to reconstruct a more accurate image.

In the third embodiment and the modification example of the third embodiment above, the examples are explained in which the correction circuitry 151 corrects the count results; however, possible embodiments are not limited to these examples. For instance, another arrangement is also acceptable in which the pre-processing circuitry 34 corrects the count results by using the correction amounts calculated by the correction amount calculation circuitry 150.

Further, in the third embodiment and the modification example of the third embodiment above, the examples are explained in which the count results are further corrected while addressing the local temperature changes in the detector 13; however, possible embodiments are not limited to these examples. For instance, it is also acceptable to reconstruct an image by correcting an impact made on the characteristics of the detector 13 by the temperature change in the detector 13, without addressing the local temperature changes in the detector 13. In that situation, the data acquisition circuitry 14b is configured so as to include the ASICs 140, the correction amount calculation circuitry 150, the correction circuitry 151, and the third correspondence information storage circuitry 152.

Fourth Embodiment

In the first to the third embodiments described above, the example is explained in which the count rates are calculated on the basis of the detection signals corresponding to the incident photons that are detected, during a main image taking process, by the ASICs 140 for each of the views in a corresponding one of the detection areas. Further, in the first to the third embodiments, the example is explained in which, during the main image taking process, the calculation circuitry 146 calculates the heat generation amount on the basis of the count rate for each of the views and each of the detection areas, so that the control circuitry 147 (or 147a) determines the control amount on the basis of the heat generation amount for each of the views and each of the detection areas and further controls the temperature by using the determined control amounts.

However, another arrangement is also acceptable in which, during a scanogram taking process (a position determining image taking process) to acquire a scanogram image (a position determining image) performed prior to the main image taking process, a count rate is calculated on the basis of the detection signals corresponding to the incident photons detected by the ASICs for each of the views and each of the detection areas, so that during the subsequent main image taking process, the calculation circuitry calculates a heat generation amount on the basis of the count rate for each of the views and each of the detection areas, and the control circuitry determines control amounts on the basis of the heat generation amounts and further controls the temperature by using the determined control amounts. This embodiment will be explained below as a fourth embodiment.

Figure 19:
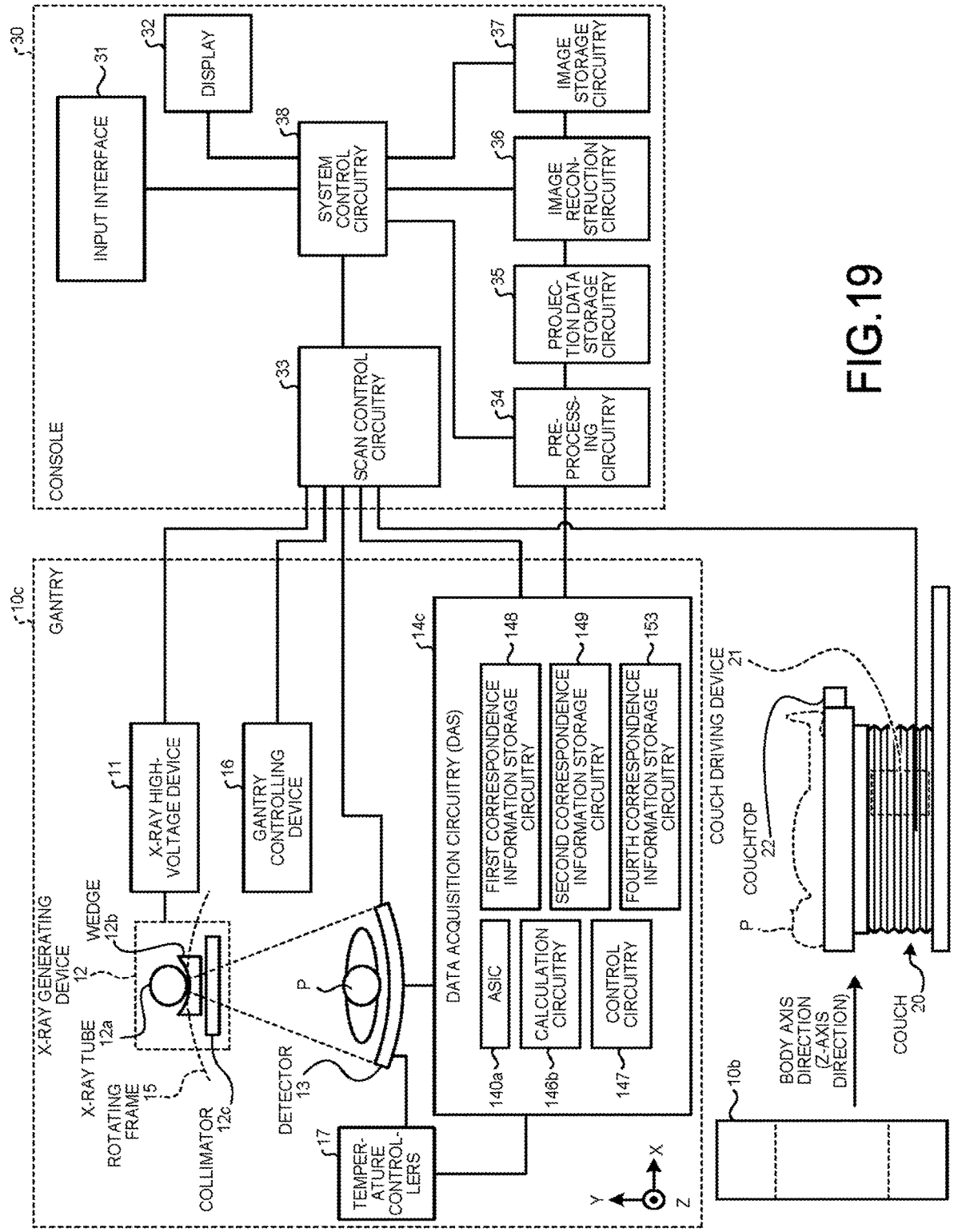
FIG. 19 is a block diagram illustrating an exemplary configuration of an X-ray CT apparatus according to a fourth embodiment.

FIG. 19 is a block diagram illustrating an exemplary configuration of an X-ray CT apparatus according to the fourth embodiment. In FIG. 19, some of the constituent elements having the same functions as those illustrated in FIG. 1 are referred to by using the same reference characters, and the detailed explanations thereof will be omitted. As illustrated in FIG. 19, the X-ray CT apparatus according to the fourth embodiment includes a gantry 10c, the couch 20, and the console 30.

The configuration of the gantry 10c is similar to that of the gantry 10 illustrated in FIG. 1, except that the configuration of data acquisition circuitry 14c is partially different from the configuration of the data acquisition circuitry 14 according to the first embodiment. Accordingly, in the following sections, only the configuration of the data acquisition circuitry 14c according to the fourth embodiment will be explained.

The data acquisition circuitry 14c includes ASICs 140a, calculation circuitry 146a, the control circuitry 147, the first correspondence information storage circuitry 148, the second correspondence information storage circuitry 149, and fourth correspondence information storage circuitry 153. The configurations of the control circuitry 147, the first correspondence information storage circuitry 148, and the second correspondence information storage circuitry 149 included in the data acquisition circuitry 14c are the same as the configurations of the control circuitry 147, the first correspondence information storage circuitry 148, and the second correspondence information storage circuitry 149 included in the data acquisition circuitry 14.

Figures 20, 21:
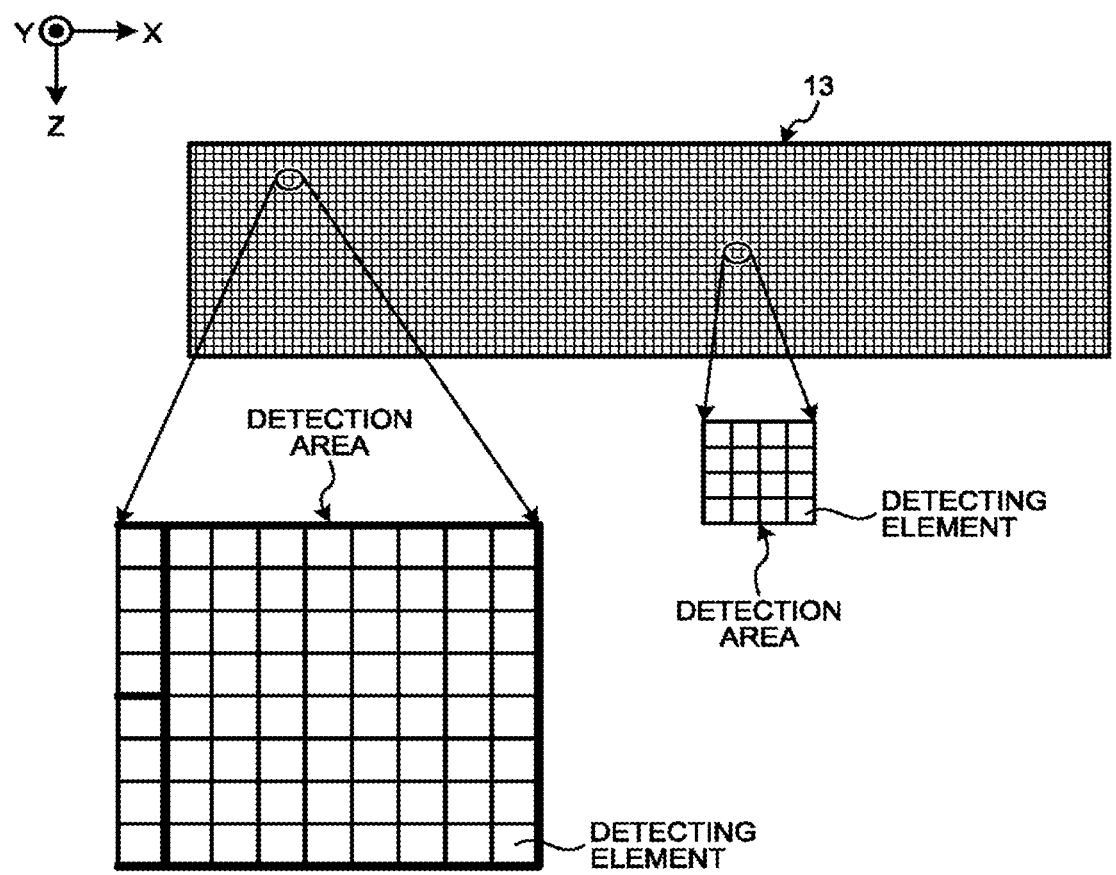
FIG. 20 is a table illustrating an example of information stored in fourth correspondence information according to the fourth embodiment.
FIG. 21 is a drawing for explaining an example of sizes of detection areas.

The fourth correspondence information storage circuitry 153 is structured by using a NAND flash memory or an HDD, for example, and is configured to store therein fourth correspondence information. FIG. 20 is a table illustrating an example of information stored in the fourth correspondence information according to the fourth embodiment. As illustrated in FIG. 20, the fourth correspondence information stores therein information in which "count rates in scanogram taking processes" and "count rates in main image taking processes" are kept in correspondence with one another. The fourth correspondence information is generated by either measuring or conjecturing from a simulation, in advance, count rates in units of the views from the detection areas of the detector 13 output from the ASICs 140a during the scanogram taking process and count rates in units of the views from the detection areas of the detector 13 output from the ASICs 140a during the main image taking process.

Each of the "count rates in scanogram taking processes" in the fourth correspondence information indicates a count result in each of the views during a scanogram taking process. For example, as the "count rates in scanogram taking processes", pieces of information such as "C<C5" indicating that the count rate is lower than C5, "C5≤C<C6" indicating that the count rate is equal to or higher than C5 but lower than C6, and the like are stored. Further, each of the "count rates in main image taking processes" in the fourth correspondence information indicates a count result in each of the views during a main image taking process. For example, as the "count rates in main image taking processes", pieces of information such as "C<C1" indicating that the count rate is lower than C1, "C1≤C<C2" indicating that the count rate is equal to or higher than C1 but lower than C2, and the like are stored. The scanogram taking process is an example of a first image taking process. The main image taking process is an example of a second image taking process.

In one example, the fourth correspondence information illustrated in FIG. 20 indicates that the count rate in a main image taking process is lower than C1 when the count rate in a scanogram taking process is lower than C5 and that the count rate in a main image taking process is equal to or higher than C1 but lower than C2 when the count rate in a scanogram taking process is equal to or higher than C5 but lower than C6.

In the fourth embodiment, the X-ray CT apparatus performs a scanogram taking process before performing the main image taking process. For example, during the scanogram taking process, the X-ray tube 12a emits X-rays that are in a smaller X-ray dose than the X-ray dose of the X-rays emitted from the X-ray tube 12a during the main image taking process. The ASICs 140a are configured to calculate the count rates on the basis of the detection signals corresponding to the incident photons detected in each of the detection areas during the scanogram taking process, by using the same method as the method used by the ASICs 140 according to the first embodiment for calculating the count rates.

During the scanogram taking process, the X-ray tube 12a emits the X-rays toward the patient P, for example, by using a single view, two views apart from each other by 90 degrees, or all views (e.g., 2,400 views).

During the scanogram taking process, when the X-rays are radiated in a single view, the ASICs 140a conjecture the count rate for this view, on the basis of the detection signals based on the X-rays radiated in the single view. Further, on the basis of the detection signals based on the X-rays radiated in the single view, the ASICs 140a conjecture the thickness of the patient P and further calculate count rates corresponding to X-ray radiations in other views by using the conjectured thickness.

During the scanogram taking process, when the X-rays are radiated in two views, the ASICs 140a calculate a count rate in each of the views, on the basis of two detection signals based on the X-rays radiated in the two views. Further, on the basis of the two detection signals, the ASICs 140a conjecture the thickness of the patient P and further conjecture the shape of the patient P on the assumption that the shape of the patient P is oval. After that, the ASICs 140a calculate count rates corresponding to X-ray radiations in other views by using the conjectured thickness and shape.

During the scanogram taking process, when the X-rays are radiated in all the views, the count rate in each of the views is calculated on the basis of the detection signals based on the X-rays radiated in the view.

After that, the ASICs 140a generate information (scanogram taking process correspondence information) in which the views corresponding to the calculated count rates, the detection areas corresponding to the calculated count rates, and the calculated count rates are kept in correspondence with one another and further stores the scanogram taking process correspondence information into a memory (not illustrated) provided in the data acquisition circuitry 14c. In this manner, during the scanogram taking process, the count rate is calculated for each of the views and each of the detection areas, according to the fourth embodiment.

Further, during the main image taking process performed after the scanogram taking process, the calculation circuitry 146a refers to the scanogram taking process correspondence information and, every time a view trigger signal is received, the calculation circuitry 146a obtains a corresponding count rate from the scanogram taking process correspondence information for each of the detection areas. In other words, the calculation circuitry 146a obtains the corresponding count rate from the scanogram taking process correspondence information for each of the views and each of the detection areas. In this situation, the count rates obtained from the scanogram taking process correspondence information are the count rates during scanogram taking processes.

After that, by referring to the fourth correspondence information, the calculation circuitry 146a obtains count rates in the main image taking process corresponding to the obtained count rates during the scanogram taking process, from the fourth correspondence information. In this manner, the calculation circuitry 146 calculates the count rate during the main image taking process, for each of the views and each of the detection areas.

Subsequently, by using the same method as the method used by the calculation circuitry 146 in any of the first to the third embodiments for calculating the heat generation amounts on the basis of the count rates, the calculation circuitry 146a according to the fourth embodiment calculates heat generation amounts on the basis of the count rates in the main image taking process. In other words, the calculation circuitry 146a calculates the heat generation amount on the basis of the count rate during the image taking process, for each of the views and each of the detection areas. In this manner, the calculation circuitry 146a calculates the heat generation amount for each of the detection areas in the main image taking process, on the basis of the detection signals corresponding to the incident photons detected in the detection areas during the scanogram taking process.

After that, by using the same method as the method used by the control circuitry 147 (or 147a) in any of the first to the third embodiments for determining the control amounts on the basis of the heat generation amounts and controlling the temperature by using the determined control amounts, the control circuitry 147 according to the fourth embodiment performs the following process. For example, the control circuitry 147 according to the fourth embodiment determines a control amount on the basis of the heat generation amount for each of the views and each of the detection areas in the main image taking process and further controls the temperature by using the determined control amounts.

The X-ray CT apparatus according to the fourth embodiment has thus been explained. In the fourth embodiment also, it is possible to address the local temperature changes in the detector 13, similarly to the first embodiment.

Other Embodiments

Possible embodiments are not limited to those described above.

In the embodiments described above, the example is explained in which the temperature controller 17 is provided for each of the detection areas, i.e., the temperature controllers 17 are provided in 1:1 correspondence with the detection areas. However, possible embodiments are not limited to this example. For instance, one temperature controller 17 may be provided for two or more detection areas. For example, when the distance between the detection areas is short, one temperature controller 17 may control the temperatures of the two or more detection areas. As another example, when the number of detecting elements contained in one detection area is large, the temperature of the one detection area may be controlled by two or more temperature controllers 17.

Further, in the embodiments described above, the example is explained in which the plurality of detection areas have the same size as one another; however, the sizes of the detection areas may vary depending on the positions thereof in at least one selected from between the channel direction and the column direction. FIG. 21 is a drawing for explaining an example of the sizes of the detection areas.

For example, as illustrated in FIG. 21, because a larger amount of X-rays passes through the patient P in a center part (a central part) of the detector 13 in the channel direction (the Z-axis direction), the sizes of the detection areas may be arranged so as to contain sixteen detecting elements corresponding to four columns by four channels.

In contrast, because a smaller amount of X-rays passes through the patient P in the periphery part of the detector 13 in the channel direction, the sizes of the detection areas may be arranged so as to contain 64 detecting elements corresponding to eight columns by eight channels.

In other words, the sizes of the detection areas may be varied in accordance with the passage amount through the patient P with respect to the X-rays becoming incident to the detection areas.

In the embodiments described above, the example is explained in which the heat discharge efficiency is different between the ASICs 140 positioned in the central part of the detector 13 and the ASICs 140 positioned in the periphery part thereof; however, possible embodiments are not limited to this example. For instance, when a plurality of cooling fans are provided in the vicinity of the DAS so that the heat discharging efficiency is similar between the ASICs 140 in the central part of the detector 13 and the ASICs 140 in the periphery part thereof, there is no need to set control amounts corresponding to each detection area. For example, in the second correspondence information illustrated in FIG. 10 and the second correspondence illustrated in FIG. 14, there is no need to keep the "detection area IDs" in correspondence therewith.

Further, in the embodiments described above, the example is explained in which the "detection area IDs" are not kept in correspondence with the third correspondence information illustrated in FIG. 18; however, possible embodiments are not limited to this example. For instance, the "detection area IDs" may further be kept in correspondence with the third correspondence information.

Further, in the embodiments described above, the example is explained in which the ASICs 140 (or 140a) are provided for the data acquisition circuitry 14 (or 14a, 14b, 14c); however, possible embodiments are not limited to this example. For instance, the ASIC 140 (or 140a) may be provided for the detector 13.

Further, in the embodiments described above, the X-ray CT apparatuses of a rotate/rotate type (third-generation CT) are explained in which the X-ray tube 12a and the detector 13 rotate around the patient P while being integrally structured; however, possible embodiments are not limited to this example. For instance, examples of X-ray CT apparatuses other than the third-generation CT include those of a stationary/rotation-type (fourth generation CT) in which an X-ray detector having a plurality of X-ray detecting elements is fixed while being arranged in a ring form in a distributed manner, so that only an X-ray tube rotates around the patient. The embodiments described above are also applicable to the fourth generation CT. Further, the embodiments described above are also applicable to hybrid X-ray CT apparatuses configured by combining together the third-generation CT and the fourth-generation CT.

Further, the embodiments described above are also applicable to conventional X-ray CT apparatuses of a single X-ray tube type and to X-ray CT apparatuses of a multiple X-ray tube type in which a plurality of pairs each made up of an X-ray tube and a detector are installed on a rotating ring.

Further, in the embodiments described above, the example is explained in which the plurality of functions are provided in the console 30 as the independent circuits so that each of the circuits implements the function thereof; however, possible embodiments are not limited to this example. For instance, another arrangement is also acceptable in which one piece of processing circuitry implements a plurality of functions. For example, the processing circuitry implements a scan controlling function, a pre-processing function, an image reconstructing function, and a system controlling function. In this situation, the processing functions implemented by the scan controlling function, the pre-processing function, the image reconstructing function, and the system controlling function, which are constituent elements of the processing circuitry, are recorded in storage circuitry in the form of computer-executable programs. The processing circuitry is structured by using a processor, for example, and by reading and executing the programs from the storage circuitry, the processing circuitry is configured to realize the functions corresponding to the read programs.

Further, for example, one piece of processing circuitry may implement the functions of the ASICs 140 (or 140a), the functions of the calculation circuitry 146 (or 146a), and the functions of the control circuitry 147 (or 147a) described above.

Further, in the embodiments above, the example is explained in which the pre-processing circuitry 34 and the image reconstruction circuitry 36 are implemented in the console 30; however, possible embodiments are not limited to this example. For instance, the pre-processing circuitry 34 and the image reconstruction circuitry 36 may be implemented by an external workstation.

Further, although the X-ray CT apparatuses are explained in the embodiments described above, possible embodiments are not limited to those examples. For instance, the embodiments described above are also applicable to mammography apparatuses and X-ray diagnosis apparatuses each including a photon counting X-ray detector. In other words, the embodiments described above are also applicable to radiation diagnosis apparatuses.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions thereof by reading and executing the programs incorporated in the circuits thereof. Alternatively, instead of incorporating the programs into the circuits of the processors, it is also acceptable to store the programs into the image storage circuitry 37 included in the console 30. In that situation, the processors realize the functions thereof by reading and executing the programs stored in the image storage circuitry 37. The processors in the present embodiments do not each necessarily have to be structured as a single circuit. It is also acceptable to structure one processor by combining together a plurality of independent circuits so as to realize the functions thereof. Further, it is also acceptable to incorporate two or more of the constituent elements illustrated in FIG. 1, 12, 15, or 19 into one processor so as to realize the functions thereof.

In the explanations of the embodiments above, the constituent elements of the apparatuses and the devices illustrated in the drawings are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

Further, it is also possible to realize the temperature controlling process described in any of the embodiments above by using software. For example, the temperature controlling process may be realized by causing a computer to execute a temperature controlling program that defies the processing procedures described in the above embodiments as being performed by the calculation circuitry 146 and the control circuitry 147. For example, the temperature controlling program may be stored in a hard disk, a semiconductor memory element, or the like and is read and executed by a processor such as a CPU, a Micro Processing Unit (MPU) or the like. The temperature controlling program may be distributed via a network such as the Internet. Further, the temperature controlling program may be distributed as being recorded onto a computer-readable recording medium such as a Compact Disk Read-Only Memory (CD-ROM), a Magnetic Optical (MO) disk, a Digital Versatile Disk (DVD), or the like.

According to at least one aspect of the embodiments described above, it is possible to address the local temperature changes in the detector.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a photon counting detector that includes a plurality of detection areas arranged in a channel direction and a column direction and is configured to output detection signals corresponding to a quantity of photons incident on the plurality of detection areas, the plurality of detection areas each including a plurality of detecting elements; and
   processing circuitry configured to calculate a heat generation amount for each detection area of the plurality of detection areas on a basis of the detection signal corresponding to the incident photons detected in the each detection area, to determine a control amount on a basis of the heat generation amount calculated for each of the plurality of detection areas, and to control temperature in each of the plurality of detection areas by using the determined control amount.
2. The X-ray CT apparatus according to claim 1, wherein the processing circuitry determines the control amounts by using the heat generation amounts and a temperature measured in a vicinity of the photon counting detector and obtained from a temperature sensor.
3. The X-ray CT apparatus according to claim 1, wherein the processing circuitry determines the control amounts corresponding to positions of the plurality of detection areas in the photon counting detector.
4. The X-ray CT apparatus according to claim 1, wherein the processing circuitry reconstructs an image by using projection data based on the detection signals.
5. The X-ray CT apparatus according to claim 1, wherein
   the processing circuitry calculates a correction amount corresponding to a temperature change in the photon counting detector, and
   the processing circuitry corrects the detection signals output by the photon counting detector by using the correction amount.
6. The X-ray CT apparatus according to claim 5, wherein the processing circuitry calculates the correction amount by conjecturing the temperature change in the photon counting detector on a basis of the control amounts and a history of count results corresponding to each view based on the detection signals from the detecting elements in each of the plurality of detection areas.
7. The X-ray CT apparatus according to claim 5, wherein the processing circuitry reconstructs an image by using projection data based on the corrected detection signals.
8. The X-ray CT apparatus according to claim 1, wherein
   on a basis of the detection signals corresponding to the incident photons detected in the plurality of detection areas during a first image taking process, the processing circuitry calculates the heat generation amount for each of the plurality of detection areas during a second image taking process performed after the first image taking process,
   the processing circuitry determines the control amounts on the basis of the heat generation amount calculated for each of the plurality of detection areas, and
   the processing circuitry controls the temperature in the plurality of detection areas by using the determined control amounts.
9. The X-ray CT apparatus according to claim 1, wherein sizes of the plurality of detection areas vary depending on positions thereof in at least one selected from between the channel direction and the column direction.
10. The X-ray CT apparatus according to claim 4, wherein
   the processing circuitry calculates a correction amount corresponding to a temperature change in the photon counting detector, and
   the processing circuitry corrects the detection signals output by the photon counting detector by using the correction amount.
11. An X-ray CT method comprising:
   detecting, using a photon counting detector that includes a plurality of detection areas arranged in a channel direction and a column direction a quantity of photons incident on the plurality of detection areas, the plurality of detection areas each including a plurality of detecting elements;
   outputting output detection signals corresponding to the detected quantity of photons incident on the plurality of detection areas;
   calculating a heat generation amount for each detection area of the plurality of detection areas on a basis of the detection signal corresponding to the incident photons detected in the each detection area;

determining a control amount on a basis of the heat generation amount calculated for each of the plurality of detection areas; and controlling temperature in each of the plurality of detection areas by using the determined control amount.

12. The X-ray CT method according to claim 11, further comprising determining the control amounts by using the heat generation amounts and a temperature measured in a vicinity of the photon counting detector and obtained from a temperature sensor.

13. The X-ray CT method according to claim 11, further comprising determining the control amounts corresponding to positions of the plurality of detection areas in the photon counting detector.

14. The X-ray CT method according to claim 11, further comprising reconstructing an image by using projection data based on the detection signals.

15. The X-ray CT method according to claim 11, further comprising:

calculating a correction amount corresponding to a temperature change in the photon counting detector, and correcting the detection signals output by the photon counting detector by using the correction amount.

16. The X-ray CT method according to claim 15, wherein calculating the correction amount comprises conjecturing the temperature change in the photon counting detector on a basis of the control amounts and a history of count results corresponding to each view based on the detection signals from the detecting elements in each of the plurality of detection areas.

17. The X-ray CT method according to claim 15, further comprising reconstructing an image by using projection data based on the corrected detection signals.

18. The X-ray CT method according to claim 11, further comprising on a basis of the detection signals corresponding to the incident photons detected in the plurality of detection areas during a first image taking process, calculating the heat generation amount for each of the plurality of detection areas during a second image taking process performed after the first image taking process, determining the control amounts on the basis of the heat generation amount calculated for each of the plurality of detection areas, and controlling the temperature in the plurality of detection areas by using the determined control amounts.

19. The X-ray CT method according to claim 11, wherein sizes of the plurality of detection areas vary depending on positions thereof in at least one selected from between the channel direction and the column direction.

20. The X-ray CT method according to claim 14, further comprising:

calculating a correction amount corresponding to a temperature change in the photon counting detector, and correcting the detection signals output by the photon counting detector by using the correction amount.

* * * * *